(12) United States Patent
Sun et al.

(10) Patent No.: US 10,363,317 B2
(45) Date of Patent: *Jul. 30, 2019

(54) OPTIMIZED IN VIVO DELIVERY SYSTEM WITH ENDOSOMOLYTIC AGENTS FOR NUCLEIC ACID CONJUGATES

(71) Applicants: ONXEO, Paris (FR); INSTITUT CURIE, Paris (FR); CENTRE NATIONAL DE LA RECHERCHE SCIENTIFIQUE, Paris (FR)

(72) Inventors: Jian-Sheng Sun, Saint Maur des Fosses (FR); Marie Dutreix, L'Hay-les-Roses (FR); Maria Quanz, Paris (FR)

(73) Assignees: ONXEO, Paris (FR); INSTITUT CURIE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/632,951

(22) Filed: Jun. 26, 2017

(65) Prior Publication Data

US 2017/0298089 A1    Oct. 19, 2017

Related U.S. Application Data

(60) Division of application No. 15/232,844, filed on Aug. 10, 2016, now Pat. No. 9,687,557, which is a continuation of application No. 14/923,482, filed on Oct. 27, 2015, now Pat. No. 9,428,538, which is a continuation of application No. 13/703,965, filed as application No. PCT/EP2011/060280 on Jun. 21, 2011, now Pat. No. 9,205,099.

(30) Foreign Application Priority Data

Jun. 22, 2010 (EP) .................................... 10166936

(51) Int. Cl.

| | |
|---|---|
| A61K 38/17 | (2006.01) |
| A61K 38/53 | (2006.01) |
| A61K 47/54 | (2017.01) |
| A61K 31/4706 | (2006.01) |
| A61K 31/7088 | (2006.01) |
| A61K 45/06 | (2006.01) |
| C07H 21/04 | (2006.01) |
| A61K 31/713 | (2006.01) |
| A61K 47/55 | (2017.01) |
| A61K 48/00 | (2006.01) |
| A61P 35/00 | (2006.01) |

(52) U.S. Cl.
CPC ........ *A61K 47/549* (2017.08); *A61K 31/4706* (2013.01); *A61K 31/7088* (2013.01); *A61K 31/713* (2013.01); *A61K 45/06* (2013.01); *A61K 47/542* (2017.08); *A61K 47/543* (2017.08); *A61K 47/551* (2017.08); *A61K 47/554* (2017.08); *A61K 48/00* (2013.01); *A61P 35/00* (2018.01); *C07H 21/04* (2013.01)

(58) Field of Classification Search
CPC ............ A61K 31/4706; A61K 31/7088; A61K 45/06; A61K 47/48046; A61K 47/48061; A61K 47/48107
USPC .............................. 514/44 R; 536/23.1, 23.2
See application file for complete search history.

(56) References Cited

U.S. PATENT DOCUMENTS

| | | | |
|---|---|---|---|
| 5,965,404 A | 10/1999 | Buschle et al. | |
| 6,420,176 B1 | 7/2002 | Liszievicz et al. | |
| 9,205,099 B2 * | 12/2015 | Sun | A61K 31/4706 |
| 9,428,538 B2 * | 8/2016 | Sun | A61K 31/4706 |
| 9,687,557 B2 * | 6/2017 | Sun | A61K 31/4706 |
| 2007/0060499 A1 | 3/2007 | Kosak | |
| 2007/0111961 A1 * | 5/2007 | Dutreix et al. | 514/44 |

FOREIGN PATENT DOCUMENTS

| | | |
|---|---|---|
| WO | WO 91/14696 | 10/1991 |
| WO | WO 95/31541 | 11/1995 |
| WO | WO 95/33061 | 12/1995 |
| WO | WO 96/41606 | 12/1996 |
| WO | WO 97/25339 | 7/1997 |
| WO | WO 00/32815 | 6/2000 |
| WO | WO 2005/040378 | 5/2005 |
| WO | WO 2008/034866 | 3/2008 |
| WO | WO 2008/084087 | 7/2008 |
| WO | WO 2009/063998 | 5/2009 |

OTHER PUBLICATIONS

Chen, Q. et al. "Lipophilic siRNAs mediate efficient gene silencing in oligodendrocytes with direct CNS Delivery" *Journal of Controlled Release*, 2010, pp. 227-232, vol. 144, XP-002601402.

Written Opinion in International Application No. PCT/EP2011/060280, dated Jul. 26, 2011, pp. 1-6.

Crooke, S. T. et al. "Pharmacokinetic Properties of Several Novel Oligonucleotide Analogs in mice" *The Journal of Pharmacology and Experimental Therapeutics*, 1996, pp. 923-937, vol. 277, No. 2.

Gamper, H. B. et al. "Facile preparation of nuclease resistant 3' modified oligodeoxynucleotides" *Nucleic Acids Research*, 1993, pp. 145-150, vol. 21, No. 1.

(Continued)

*Primary Examiner* — Janet L Epps-Smith
(74) *Attorney, Agent, or Firm* — Saliwanchik, Lloyd & Eisenschenk

(57) ABSTRACT

The present invention relates to an optimized in vivo delivery system with endosomolytic agents for nucleic acid of therapeutic interest conjugated to molecules facilitating endocytosis, in particular for use in the treatment of cancer.

15 Claims, 7 Drawing Sheets
(2 of 7 Drawing Sheet(s) Filed in Color)
Specification includes a Sequence Listing.

(56) References Cited

OTHER PUBLICATIONS

U.S. Appl. No. 15/232,844, filed Aug. 10, 2016, now allowed.
U.S. Appl. No. 14/923,482, filed Oct. 27, 2015, now U.S. Pat. No. 9,428,538.
U.S. Appl. No. 13/703,965, now U.S. Pat. No. 9,205,099, which entered the U.S. national stage on Feb. 5, 2013, from international application No. PCT/EP2011/060280, filed Jun. 21, 2011.

* cited by examiner

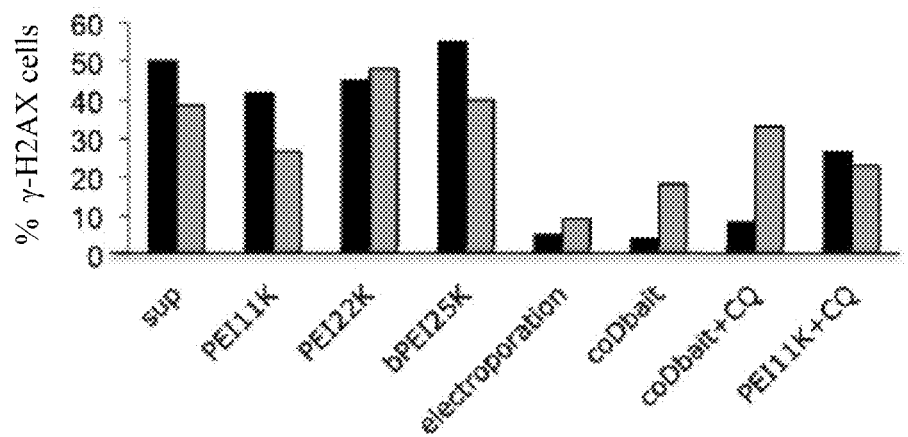
Figure 2C
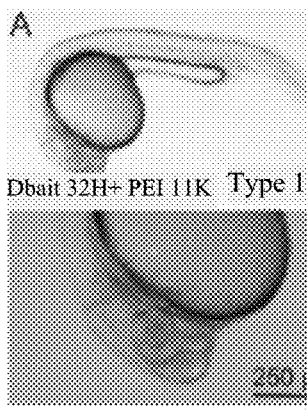
Dbait 32H+ PEI 11K Type 1
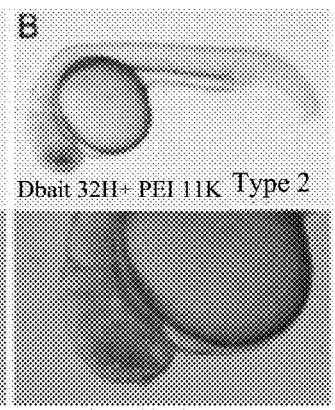
Dbait 32H+ PEI 11K Type 2
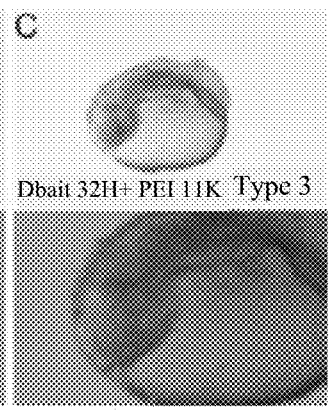
Dbait 32H+ PEI 11K Type 3
Figure 3A    Figure 3B    Figure 3C

SEQUENCE LISTING

<160> NUMBER OF SEQ ID NOS: 29

<210> SEQ ID NO 1
<211> LENGTH: 32
<212> TYPE: DNA
<213> ORGANISM: artificial sequence
<220> FEATURE:
<223> OTHER INFORMATION: Dbait32

<400> SEQUENCE: 1
acgcacgggt gttgggtcgt ttgttcggat ct                                32

<210> SEQ ID NO 2
<211> LENGTH: 32
<212> TYPE: DNA
<213> ORGANISM: artificial sequence
<220> FEATURE:
<223> OTHER INFORMATION: Dbait32Ha

<400> SEQUENCE: 2
cgtaggtctg tttggtggct ttgcagtggc ac                                32

<210> SEQ ID NO 3
<211> LENGTH: 32
<212> TYPE: DNA
<213> ORGANISM: artificial sequence
<220> FEATURE:
<223> OTHER INFORMATION: Dbait32Hb

<400> SEQUENCE: 3
gctaggcttg tttgctgggt tgtaggcaca gc                                32

<210> SEQ ID NO 4
<211> LENGTH: 32
<212> TYPE: DNA
<213> ORGANISM: artificial sequence
<220> FEATURE:
<223> OTHER INFORMATION: Dbait32Hc

<400> SEQUENCE: 4
gctgtgccca aacccagca aacaagccta ga                                 32

<210> SEQ ID NO 5
<211> LENGTH: 32
<212> TYPE: DNA
<213> ORGANISM: artificial sequence
<220> FEATURE:
<223> OTHER INFORMATION: Dbait32Hd

<400> SEQUENCE: 5
gctaggtctg tttggtggct ttgcagtggc ac                                32

<210> SEQ ID NO 6
<211> LENGTH: 21
<212> TYPE: DNA
<213> ORGANISM: artificial sequence
<220> FEATURE:
<223> OTHER INFORMATION: siRNA

<400> SEQUENCE: 6
caacaagaag acgcgaauct t                                            21

<210> SEQ ID NO 7
<211> LENGTH: 21
<212> TYPE: DNA
<213> ORGANISM: artificial sequence
<220> FEATURE:
<223> OTHER INFORMATION: siRNA

<400> SEQUENCE: 7
gauucgcguc uucuuguugt t                                            21

<210> SEQ ID NO 8
<211> LENGTH: 32
<212> TYPE: DNA

```
<213> ORGANISM: artificial sequence
<220> FEATURE:
<223> OTHER INFORMATION: nucleic acid molecule Ia
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 8
acgcacgggt gttgggtcgt tgttcggat ct                                      32

<210> SEQ ID NO 9
<211> LENGTH: 32
<212> TYPE: DNA
<213> ORGANISM: artificial sequence
<220> FEATURE:
<223> OTHER INFORMATION: nucleic acid molecule Ib
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or pr

<400> SEQUENCE: 9
cgtaggtctg tttggtggct tgcagtggc ac                                      32

<210> SEQ ID NO 10
<211> LENGTH: 32
<212> TYPE: DNA
<213> ORGANISM: artificial sequence
<220> FEATURE:
<223> OTHER INFORMATION: nucleic acid molecule Ic
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
```

```
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or pr

<400> SEQUENCE: 10
gctaggcttg tttgctgggt tgtaggcaca gc                                        32

<210> SEQ ID NO 11
<211> LENGTH: 32
<212> TYPE: DNA
<213> ORGANISM: artificial sequence
<220> FEATURE:
<223> OTHER INFORMATION: nucleic acid molecule Id
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or pr

<400> SEQUENCE: 11
gctgtgccca caacccagca aacaagccta ga                                        32

<210> SEQ ID NO 12
<211> LENGTH: 32
<212> TYPE: DNA
<213> ORGANISM: artificial sequence
<220> FEATURE:
<223> OTHER INFORMATION: nucleic acid molecule Ie
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate or methylphosphonate
      backbone
```

```
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or pr

<400> SEQUENCE: 12
gctaggtctg tttggtggct ttgcagtggc ac                                    32

<210> SEQ ID NO 13
<211> LENGTH: 32
<212> TYPE: DNA
<213> ORGANISM: artificial sequence
<220> FEATURE:
<223> OTHER INFORMATION: nucleic acid molecule IIa
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 13
acgcacgggt gttgggtcgt ttgttcggat ct                                    32

<210> SEQ ID NO 14
<211> LENGTH: 32
<212> TYPE: DNA
<213> ORGANISM: artificial sequence
<220> FEATURE:
<223> OTHER INFORMATION: nucleic acid molecule IIb
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
```

```
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 14
cgtaggtctg tttggtggct ttgcagtggc ac                                      32

<210> SEQ ID NO 15
<211> LENGTH: 32
<212> TYPE: DNA
<213> ORGANISM: artificial sequence
<220> FEATURE:
<223> OTHER INFORMATION: nucleic acid molecule IIc
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 15
gctaggcttg tttgctgggt tgtaggcaca gc                                      32

<210> SEQ ID NO 16
<211> LENGTH: 32
<212> TYPE: DNA
<213> ORGANISM: artificial sequence
<220> FEATURE:
<223> OTHER INFORMATION: nucleic acid molecule IId
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 16
```
gctgtgccca caacccagca aacaagccta ga        32

<210> SEQ ID NO 17
<211> LENGTH: 32
<212> TYPE: DNA
<213> ORGANISM: artificial sequence
<220> FEATURE:
<223> OTHER INFORMATION: nucleic acid molecule IIe
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 17
gctaggtctg tttggtggct ttgcagtggc ac        32

<210> SEQ ID NO 18
<211> LENGTH: 32
<212> TYPE: DNA
<213> ORGANISM: artificial sequence
<220> FEATURE:
<223> OTHER INFORMATION: nucleic acid molecule IIIa
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 18
acgcacgggt gttgggtcgt ttgttcggat ct        32

<210> SEQ ID NO 19

```
<211> LENGTH: 32
<212> TYPE: DNA
<213> ORGANISM: artificial sequence
<220> FEATURE:
<223> OTHER INFORMATION: nucleic acid molecule IIIb
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 19
cgtaggtctg tttggtggct ttgcagtggc ac                                    32

<210> SEQ ID NO 20
<211> LENGTH: 32
<212> TYPE: DNA
<213> ORGANISM: artificial sequence
<220> FEATURE:
<223> OTHER INFORMATION: nucleic acid molecule IIIc
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 20
gctaggcttg tttgctgggt tgtaggcaca gc                                    32

<210> SEQ ID NO 21
<211> LENGTH: 32
<212> TYPE: DNA
<213> ORGANISM: artificial sequence
<220> FEATURE:
<223> OTHER INFORMATION: nucleic acid molecule IIId
```

```
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 21
gctgtgccca aacccagca aacaagccta ga                                   32

<210> SEQ ID NO 22
<211> LENGTH: 32
<212> TYPE: DNA
<213> ORGANISM: artificial sequence
<220> FEATURE:
<223> OTHER INFORMATION: nucleic acid molecule IIIe
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 22
gctaggtctg tttggtggct ttgcagtggc ac                                  32

<210> SEQ ID NO 23
<211> LENGTH: 32
<212> TYPE: DNA
<213> ORGANISM: artificial sequence
<220> FEATURE:
<223> OTHER INFORMATION: nucleic acid molecule DT01
<220> FEATURE:
<221> NAME/KEY: misc_feature
<223> OTHER INFORMATION: note="at the 3' end of the complementary strand
      the three last nucleotides with phosphorothioate backbone"
<220> FEATURE:
```

```
<221> NAME/KEY: misc_feature
<222> LOCATION: (1)..(1)
<223> OTHER INFORMATION: at the 5' end,
      10-O-[1-propyl-3-N-carbamoylcholesteryl]-triethyleneglycol
      radical
<220> FEATURE:
<221> NAME/KEY: modified_base
<222> LOCATION: (1)..(3)
<223> OTHER INFORMATION: mod_base= phosphorothioate  backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =
      2,19-bis(phosphor)-8-hydraza-1-hydroxy-4-oxa-9-oxo-nonadecane

<400> SEQUENCE: 23
gctgtgccca acccagca aacaagccta ga                                    32

<210> SEQ ID NO 24
<211> LENGTH: 32
<212> TYPE: DNA
<213> ORGANISM: artificial sequence
<220> FEATURE:
<223> OTHER INFORMATION: nucleic acid molecule IIa
<220> FEATURE:
<221> NAME/KEY: modified_base
<222> LOCATION: (30)..(32)
<223> OTHER INFORMATION: mod_base = phosphorothioate or
      methylphosphonate backbone

<400> SEQUENCE: 24
agatccgaac aaacgaccca acacccgtgc gt                                  32

<210> SEQ ID NO 25
<211> LENGTH: 32
<212> TYPE: DNA
<213> ORGANISM: artificial sequence
<220> FEATURE:
<223> OTHER INFORMATION: nucleic acid molecule IIb
<220> FEATURE:
<221> NAME/KEY: modified_base
<222> LOCATION: (30)..(32)
<223> OTHER INFORMATION: mod_base = phosphorothioate or
      methylphosphonate backbone

<400> SEQUENCE: 25
gtgccactgc aaagccacca aacagaccta cg                                  32

<210> SEQ ID NO 26
<211> LENGTH: 32
<212> TYPE: DNA
<213> ORGANISM: artificial sequence
<220> FEATURE:
<223> OTHER INFORMATION: nucleic acid molecule IIc
<220> FEATURE:
<221> NAME/KEY: modified_base
<222> LOCATION: (30)..(32)
<223> OTHER INFORMATION: mod_base = phosphorothioate or
      methylphosphonate backbone

<400> SEQUENCE: 26
gctgtgccta acccagca aacaagccta gc                                    32

<210> SEQ ID NO 27
<211> LENGTH: 32
<212> TYPE: DNA
<213> ORGANISM: artificial sequence
<220> FEATURE:
```

```
<223> OTHER INFORMATION: nucleic acid molecule IId
<220> FEATURE:
<221> NAME/KEY: modified_base
<222> LOCATION: (30)..(32)
<223> OTHER INFORMATION: mod_base = phosphorothioate or
      methylphosphonate backbone

<400> SEQUENCE: 27
tctaggcttg tttgctgggt tgtgggcaca gc                                32

<210> SEQ ID NO 28
<211> LENGTH: 32
<212> TYPE: DNA
<213> ORGANISM: artificial sequence
<220> FEATURE:
<223> OTHER INFORMATION: nucleic acid molecule IIe
<220> FEATURE:
<221> NAME/KEY: modified_base
<222> LOCATION: (30)..(32)
<223> OTHER INFORMATION: mod_base = phosphorothioate or
      methylphosphonate backbone

<400> SEQUENCE: 28
gtgccactgc aaagccacca aacagaccta gc                                32

<210> SEQ ID NO 29
<211> LENGTH: 32
<212> TYPE: DNA
<213> ORGANISM: artificial sequence
<220> FEATURE:
<223> OTHER INFORMATION: nucleic acid molecule DT01 (from SEQ 23) or
      Dbait32HC (from SEQ 4)
<220> FEATURE:
<221> NAME/KEY: modified_base
<222> LOCATION: (30)..(32)
<223> OTHER INFORMATION: mod_base = phosphorothioate backbone

<400> SEQUENCE: 29
tctaggcttg tttgctgggt tgtgggcaca gc                                32
```

OPTIMIZED IN VIVO DELIVERY SYSTEM WITH ENDOSOMOLYTIC AGENTS FOR NUCLEIC ACID CONJUGATES

CROSS-REFERENCE TO RELATED APPLICATIONS

This application is a divisional of U.S. application Ser. No. 15/232,844, filed Aug. 10, 2016, now U.S. Pat. No. 9,687,557, which is a continuation of U.S. application Ser. No. 14/923,482, filed Oct. 27, 2015, now U.S. Pat. No. 9,428,538, which is a continuation of U.S. application Ser. No. 13/703,965, filed Feb. 5, 2013, now U.S. Pat. No. 9,205,099, which is the U.S. national stage application of International Patent Application No. PCT/EP2011/060280, filed Jun. 21, 2011.

The Sequence Listing for this application is labeled "Seq-List.txt" which was created on Oct. 22, 2014 and is 19 KB. The entire content of the sequence listing is incorporated herein by reference in its entirety.

FIELD OF THE INVENTION

The present invention relates to the field of medicine, in particular oncology.

BACKGROUND OF THE INVENTION

Cancer treatment mainly consists of surgery wherever possible, cytotoxic agents such as chemotherapy, and radiotherapy. Molecular therapies for cancer treatment have emerged in the last decade, such as monoclonal antibodies targeting the cell membrane receptors, and inhibitors of tyrosine kinase receptors and other kinases which target signal transduction involved in cell proliferation, death and survival. As cytostatic agents, their monotherapy regimen often lacks sufficient clinical benefit. Synergistic outcomes are often obtained by combination with cytotoxic agents but are limited by their cumulative side effects.

Most cancer treatments directly or indirectly cause DNA damage in the treated proliferating tumor cells, which ultimately leads to their death. However, several intrinsic and acquired resistances of tumors to these treatments are, at least in part, due to the tumor cells' efficient DNA repair activities. It is now well recognized that DNA repair is an important target for cancer therapy (Helleday et al. Nat. Rev. Cancer, 2008, 8:193-204). The most advanced drug development in this field is the inhibitors of PARP.

As DNA repair is an essential survival process across all living kingdom, it has multiple specialized repair pathways, and has some redundancies that make the process robust when one pathway is deficient or blocked by a therapeutic agent, such as a DNA repair inhibitor. Therefore, instead of targeting a key gene/protein involved in the DNA repair process, whatever its biological importance and clinical relevance, the innovative molecular therapy must deal with one or several key pathways as a global target, in conjunction with conventional therapies, so as to reach the most efficient cancer treatment.

It was conceived to globally target DNA lesions' sensing, signaling and repair pathways in order to disable cancers' defense to existing treatments. One strategy consists of introducing short modified DNA molecules mimicking double strand breaks (DSB), named Dbait, into cells that until then could efficiently repair DSB and thus survive. The antitumor efficacy of Dbait in association with radiotherapy (RT) or chemotherapy (CT) is explained by the fact that Dbait molecules trap the initial DSB sensing complexes, jam downstream repair signaling, subsequently disorganize all DSB repair systems (both Non-Homologous End Joining and Homologous Recombination pathways), and finally inhibit DSB repair (WO2005/040378; WO2008/034866; Quanz et al., 2009, Clinical Cancer Research 15:1308; Quanz et al., 2009, PLoS ONE 4:e6298; Dutreix et al., 2010, Mut. Res. 704:182). Ultimately, the cancer cells can no more escape their death. Dbait molecules have also been found to be effective alone, without combination with radiotherapy (RT) or chemotherapy (CT) (WO2008/084087).

However, once active agents of clinical interest are identified, the recurrent problem is to find the best way to deliver the active agents, especially for nucleic acid agents. The development and optimization of efficient non-viral DNA/RNA delivery systems has to address the toxicity issues; the "tissue and systemic barriers" such as degradation, opsonization of particles by charged serum components, rapid clearing and accumulation in non-target tissues when the active substance is administered by systemic route; and the "cellular barriers" to their delivery such as low uptake across the cytoplasmic membrane, inadequate release of DNA molecules in the active cellular compartments, and lack of nuclear targeting (required for gene therapy).

Indeed, to be effective, most of these active agents have to be taken up by the cells and to reach the cytoplasm and/or nucleus. In particular, when active agents including nucleic acids are administered in their "free" or naked form, they frequently suffer from degradation before and after uptake by target cells. Inside the cells, this degradation is mainly due to the fact that nucleic acids enter cells by endocytosis, and are sequestered in cellular endosomes that ultimately evolve into the lysosomes where chemical and enzymatic degradation is very efficient.

In the prior art, active agents have been conjugated to various carriers and have been encapsulated into liposomes, micelles and nanoparticles where they are protected from degradation in serum. The prior art also employs a variety of chemistries for covalent coupling of nucleic acids and other active agents to molecular carriers that include polymers such as dextrans or PEG or molecules aiming to decrease clearance, carriers including transferrin, and lipophilic molecules such as cholesterol linked to siRNA to enhance cellular uptake (Chen et al., 2010, J. Controlled Release 144:227). Such carriers may include targeting moieties such as antibodies, polypeptides, nucleic acids and other substances to direct the active agents to selected target cells. The prior art also discloses molecules improving endocytosis for use in pharmaceutical composition (US2008/0194540).

However, when active DNA/RNA are agents uptaken by cells through the endocytosis process, they frequently end up sequestered in endosomes where they are unable to escape, therefore greatly reducing their therapeutic potential. For instance, Zimmermann et al. showed that a cholesterol-siRNA (ApoB-1) conjugate is about 1000-fold less potent than its liposomal formulation (SNALP vector) in mice: 100 mg/kg of chol-siApoB-1 is equivalent to 0.1 mg/kg of SNALP-ApoB-1 (Zimmermann et al., Nature, 2006, 441:111-114, supplementary FIG. 1).

For nucleic acids, the prior art has tried to solve this problem through the use of cationic polymers such as polyethylenimine (PEI) (WO96/02655), liposomes with fusogenic lipids or peptides such as SNALP vector. PEI is able to destabilize endosomes by a well-described proton sponge effect and therefore facilitate the release of the nucleic acid. However, the use of PEI is often limited by its cytotoxicity and so far has not been approved for use in humans. Liposomal formulation also exhibits toxicity and limited encapsulation of nucleic acids (usually in the range of 1-2 mg/mL) that may not be suitable for the application that requires high payload of nucleic acid agents.

"Endosomolytic" agents such as chloroquines are known to enhance the transfection of nucleic acids by facilitating their escape from endosomes into the cytoplasma in cultured cells. However, the use of chloroquine is limited to in vitro use and has only rarely been evaluated for assisting nucleic acid delivery in vivo. This may be due to reports in the art at nucleic acids that teach away from its in vivo use due to chloroquine toxicity.

Benns, et al. (2000, *Bioconj. Chem.* 11: 637) reported that "Although chloroquine has proven to aid in the release of the plasma DNA into the cytoplasm, it has been found to be toxic and thus cannot be used in vivo". This problem is partly due to the fact that relatively high concentrations of free chloroquine are needed to reach the same site as the nucleic acid (i.e., plasmid DNA) in the endosome. Similarly, Zhang et al. (2003, *Gene Med* 5:209) studied in vivo use of chloroquine for gene delivery to the liver. In this article, they used a plasmid together with a peptide (polylysine/molossin) as a DNA vector. They concluded that, despite chloroquine being effective for promoting gene delivery to the liver, multiple dosing is required and its use is limited by systemic toxicity. Indeed, they demonstrated that the acute systemic chloroquine toxicity limits in vivo use to levels which are substantially below those required for optimal gene delivery. Local delivery of chloroquine is also limited by local toxicity of chloroquine and by its diffusion away from the site of delivery. Finally, they did not observe a gene delivery, or a very low level, when naked DNA is used.

In this context, WO2007/040469 discloses that the solution to the problem of the high necessary concentration of chloroquine may be overcome by covalently coupling the chloroquine to the active agent, thereby reducing the overall dosage needed. WO2009/126933 proposes to covalently link the nucleic acid to deliver both to an endosomolytic agent and to a targeting ligand.

Chloroquine and its derivatives such as hydroxychloroquine are used in curative and prophylactic treatment of malaria. It has also been studied for use in combination with radiotherapy and/or chemotherapy of cancers (Sotelo et al., 2006, *Ann Intern Med* 144:337-342; NCT01023477 and NCT00969306). The hypothesis is that chloroquine/hydroxychloroquine inhibits autophagy, which is a normal cell defense process, by exporting therapeutic agents to lysosomes where they are degraded.

In conclusion, optimization of nucleic acid-based therapies requires further addressing the efficiency and cytotoxicity of synthetic DNA delivery systems.

SUMMARY OF THE INVENTION

The present invention provides a new efficient method for in vivo delivery of nucleic acids of therapeutic interest based on the covalent conjugation of nucleic acids of therapeutic interest with a molecule facilitating endocytosis, and the use of conjugated nucleic acids of therapeutic interest in combination with an endosomolytic agent. In particular, this in vivo delivery system is used for Dbait molecules.

Therefore, the present invention relates to a pharmaceutical composition comprising a conjugated nucleic acid molecule having at least one free end and a DNA double-stranded portion of 20-200 bp with less than 60% sequence identity to any gene in a human genome, said nucleic acid molecule being covalently linked to a molecule facilitating endocytosis selected from a lipophilic molecule or a ligand which targets cell receptors enabling receptor-mediated endocytosis, and a quinoline endosomolytic agent. The pharmaceutical composition may further comprise a DNA-damaging antitumoral agent.

The present invention also relates to a product comprising a conjugated nucleic acid molecule having at least one free end and a DNA double-stranded portion of 20-200 bp with less than 60% sequence identity to any gene in a human genome, said nucleic acid molecule being covalently linked to a molecule facilitating endocytosis selected from a lipophilic molecule or a ligand which targets cell receptors enabling receptor-mediated endocytosis, and a quinoline endosomolytic agent, as a combined preparation for simultaneous, separate or sequential use. The product may further comprise a DNA-damaging antitumoral agent. Preferably, the quinoline endosomolytic agent is to be administered before and/or simultaneously with the conjugated nucleic acid molecule. In particular, the quinoline endosomolytic agent is to be administered as a pre-treatment of at least one week by the oral route, and then the conjugated nucleic acid molecule and the quinoline endosomolytic agent are to be administered as a combined preparation for simultaneous, separate or sequential use.

The present invention relates to the pharmaceutical composition or product as disclosed herein for use in the treatment of cancer. Preferably, the treatment further comprises radiotherapy or chemotherapy, preferably with a DNA-damaging antitumoral agent. Optionally, the DNA-damaging antitumoral agent is selected from the group consisting of an inhibitor of topoisomerases I or II, a DNA crosslinker, a DNA alkylating agent, an anti-metabolic agent and inhibitors of the mitotic spindles.

In a preferred embodiment, the quinoline endosomolytic agent is chloroquine or hydroxychloroquine, preferably chloroquine.

In a preferred embodiment, the molecule facilitating endocytosis is selected from the group consisting of single or double chain fatty acids such as octodecyl and dioleoyl, tocopherol, folates or folic acid, cholesterol, sugars such as galactose and mannose and their oligosaccharides, peptides such as RGD and bombesin, and proteins such as integrin, preferably single or double chain fatty acids, folates and cholesterol, more preferably dioleoyl, octadecyl, folic acid, and cholesterol, still more preferably cholesterol.

In a preferred embodiment, the conjugated nucleic acid molecule has one of the following formulae:

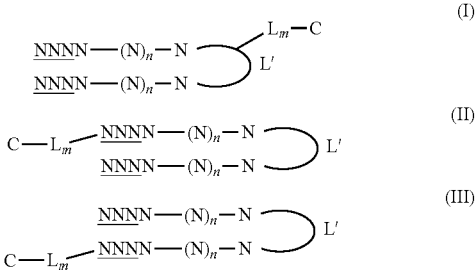

wherein N is a nucleotide, n is an integer from 15 to 195, the underlined N refers to a nucleotide having or not having a modified phosphodiester backbone, L' is a linker, C is the molecule facilitating endocytosis, L is a linker, and m is an integer being 0 or 1. Preferably, the underlined N refers to a nucleotide having a modified phosphodiester backbone.

Preferably, the linker L' is selected from the group consisting of hexaethyleneglycol, tetradeoxythymidylate (T4) and 2,19-bis(phosphor)-8-hydraza-1-hydroxy-4-oxa-9-oxo-nonadecane; and/or m is 1 and L is a carboxamido oligoethylene glycol, preferably a carboxamido triethylene glycol; and/or C is selected from the group consisting of single or double chain fatty acids, folates and cholesterol. More preferably, the linker L' is selected from the group consisting of hexaethyleneglycol, tetradeoxythymidylate (T4) and 2,19-bis(phosphor)-8-hydraza-1-hydroxy-4-oxa-9-oxo-nonadecane; and m is 1 and L is a carboxamido oligoethylene glycol, preferably a carboxamido triethylene glycol; and C is selected from the group consisting of single or double chain fatty acids, tocopherol, folates or folic acid, cholesterol, sugars such as galactose and mannose and their oligosaccharides, peptides such as RGD and bombesin, and proteins such as integrin, preferably single or double chain fatty acids, folates and cholesterol. More preferably, C is selected from the group consisting of dioleoyl, octadecyl, folic acid, and cholesterol. Still more preferably C is cholesterol.

In a more particular embodiment, the conjugated nucleic acid molecule has one of the following formulae:

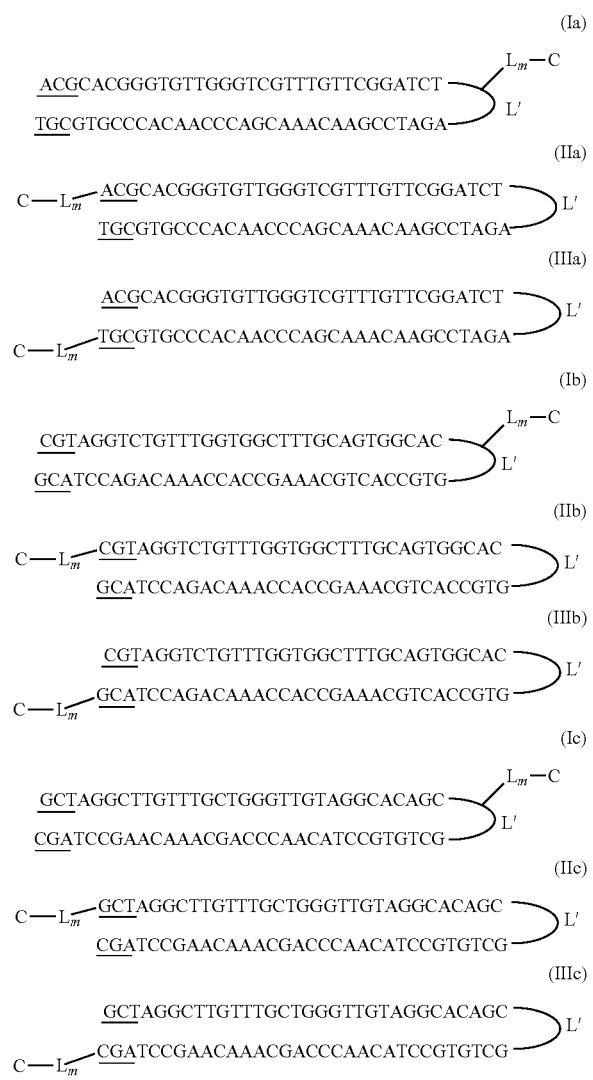

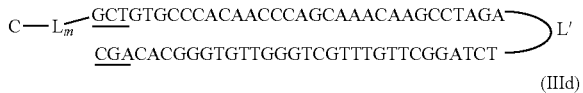

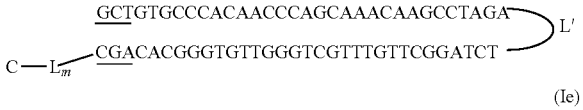

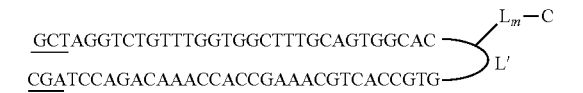

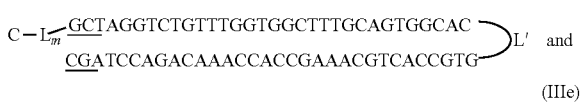

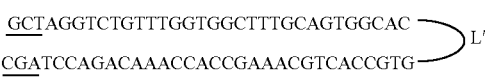

wherein the underlined nucleotide refers to a nucleotide having or not having a phosphorothioate or methylphosphonate backbone, L' is a linker, C is the molecule facilitating endocytosis, L is a linker, and m is an integer being 0 or 1. Preferably, the underlined nucleotide refers to a nucleotide have a phosphorothioate or methylphosphonate backbone. Preferably, the underlined nucleotide refers to a nucleotide having a phosphorothioate backbone; and/or the linker L' is selected from the group consisting of hexaethyleneglycol, tetradeoxythymidylate (T4) and 2,19-bis(phosphor)-8-hydraza-1-hydroxy-4-oxa-9-oxo-nonadecane; and/or m is 1 and L is a oligoethylene glycol, preferably a carboxamido triethyleneglycol, carboxamido tetraethyleneglycol, or carboxamido oligoethylene glycol, more preferably a carboxamido triethylene glycol; and/or C is selected from the group consisting of single or double chain fatty acids, tocopherol, folates or folic acid, cholesterol, sugars such as galactose and mannose and their oligosaccharides, peptides such as RGD and bombesin, and proteins such as integrin, preferably single or double chain fatty acids, folates and cholesterol. More preferably, the linker L' is selected from the group consisting of hexaethyleneglycol, tetradeoxythymidylate (T4) and 2,19-bis(phosphor)-8-hydraza-1-hydroxy-4-oxa-9-oxo-nonadecane; and m is 1 and L is a carboxamido polyethylene glycol, preferably a carboxamido triethylene glycol; and C is selected from the group consisting of single or double chain fatty acids, folates and cholesterol. More preferably, C is selected from the group consisting of dioleoyl, octadecyl, folic acid, and cholesterol. Still more preferably, C is cholesterol.

In a very specific embodiment, the conjugated nucleic acid molecule is

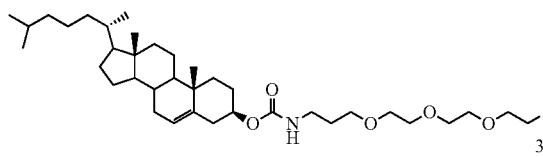

wherein the underlined nucleotide refers to a nucleotide having a phosphorothioate backbone.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 2A-2C: Activity of formulated Dbait. (A) DNA-PK activation was measured after addition of 50 u purified enzyme complex to no DNA, 0.25 μg Dbait or 0.25 μg coDbait. (B) Immunodetection of γ-H2AX in cells 24 hours after treatment with 1.6 μg/ml Dbait (left), 1.6 μg/ml Dbait/PEI11K (middle), 16 μg/ml coDbait with CQ. Scale bar: 20 μm. (C) Quantification of γ-H2AX, 5 hours (black) and 24 hours (grey) after treatment by various formulated Dbait. All transfections were performed with 1.6 μg/mL Dbait or 16 μg/mL coDbait. When indicated, CQ was added prior to transfection.

FIGS. 3A-3D: Phenotypes 24 hours after Dbait injection into the extracellular space of cell stage 1K zebrafish embryos. (A-C) Lateral views anterior to the left of zebrafish embryos 24 hours after Dbait-cy3+PEI injection (2-5 nL) at the animal pole of cell stage 1K zebrafish embryos: top panel, bright field view; bottom panel, 2× magnification of the head region with epifluorescence overlay showing in red Dbait-cy3. (A) Type 1 phenotype undistinguishable from non-injected (not shown). (B) Type 2 mild phenotype with extensive cell death in the head region. (C) Type 3 strong teratogenesis and widespread cell death. (D) Histogram showing the percentage of the three phenotypic classes depending on the adjuvant. More than 100 embryos were analyzed for each condition. NA: Dbait injected alone; Sup: SuperFect; 25 k, 22 k, 11 k PEI of the corresponding size; chloro: chloroquine; Lut: Lutrol.

DETAILED DESCRIPTION OF THE INVENTION

Figure 1A:
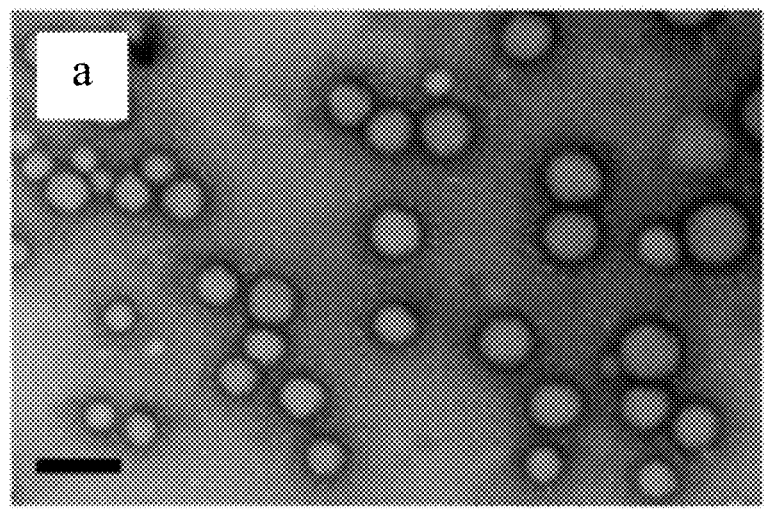
FIGS. 1A-1B: Cellular uptake of formulated Dbait. (A) Microscopy analysis of Dbait complexes with PEI11k (a). (B) Flow cytometry analysis of cellular uptake was performed 5 hours after beginning of treatment for various transfection conditions. Dbait-cy3 with SuperFect, 2 μg/ml coDbait-cy3 without and with chloroquine treatment prior transfection, 25 μg/ml coDbait-cy3 without and with CQ.

Introducing small DNA molecules (Dbait) impairs DNA repair of damaged chromosomes and provides an efficient method for enhancing radiotherapy or chemotherapy efficiency in tumors, in particular in resistant tumors. However, the sensitizing activity of the Dbait molecules depends upon the efficiency of their delivery within the tumoral cells.

Therefore, the inventors compared different strategies to improve this key step. In order to test the strategies, they developed a pipeline of assays: (i) molecular analysis of complexes formed with Dbait molecules, (ii) cellular tests for Dbait uptake and activity, and (iii) live zebrafish embryo confocal microscopy monitoring for in vivo distribution and biological activity of the formulated molecules. These tests allowed the selection of the most efficient formulations and administration protocols before assays on xenografted tumours on mice. Two classes of formulation were compared: polycationic polymers with linear or branched polyethylenimine (PEI), and Dbait covalently attached cholesterol (coDbait). The linear PEI complexes were the most efficient for Dbait transfection in vitro and in vivo but displayed high toxicity. Indeed, 10-fold higher doses of coDbait used with 1 mg chloroquine (according to allometric conversion, equivalent to the prophylactic dose used in humans) were required to observe the same antitumoral effect on xenografted melanomas than Dbait when formulated with PEI. However, the tested doses of coDbait administered with chloroquine were found to be non-toxic.

Accordingly, the present invention describes the combination and the administration protocol of a cholesterol-nucleic acid conjugate with systemically administered chloroquine at clinically relevant doses, in particular the use of a cholesterol-Dbait conjugate with a prophylactic dose of chloroquine (by allometric conversion into animals), without notable toxicity. The inventors showed that a 10-fold higher amount (10×) of cholesterol-Dbait has similar potency as compared to 1× Dbait vectorized by a non-viral vector system in mice, instead of 1000-fold without the use of chloroquine as described in the prior art. This makes the conjugation of therapeutic nucleic acids to a lipophilic or cell-targeting agent a safe and economically usable delivery system.

Accordingly, despite the need of a higher dose of coDbait, the inventors surprisingly found that:

1) The combination of coDbait with chloroquine presents low, if any, toxicity in vivo. It allows to improve the therapeutic index (ratio of efficacy dose/toxicity dose) from almost 1 for Dbait/PEI to >20 for coDbait; the absence of toxicity has been observed after intravenous injection, subcutaneous injection and even after intracerebral injection in mouse, rat, rabbit and monkey.
2) The combination of coDbait with chloroquine gives a retarded and sustained activation of DNA-PK (the main target of Dbait) and allows a prolonged therapeutic effect. More particularly, an increasing activity or effect is observed through the time period.
3) Surprisingly, the coDbait is well diffused in tumor/tissue compared with Dbait/PEI.
4) For the first time, the inventors observed that chloroquine allows the cellular uptake increase of coDbait, whereas this effect is less pronounced with cholesterol conjugated to siRNA molecules.

Based on these observations, the present invention relates to:
a pharmaceutical composition comprising a) a conjugated Dbait molecule or hairpin nucleic acid molecule as described below, and optionally b) a DNA-damaging anti-tumoral agent, and a pharmaceutically acceptable carrier, in particular for use in the treatment of cancer;
a pharmaceutical composition comprising a) a conjugated Dbait molecule or hairpin nucleic acid molecule as described below, b) an endosomolytic agent as described below, and optionally c) a DNA-damaging anti-tumoral agent, and a pharmaceutically acceptable carrier, in particular for use in the treatment of cancer;
a product or kit containing a) a conjugated Dbait molecule or hairpin nucleic acid molecule as disclosed below, and optionally b) a DNA-damaging anti-tumoral agent, as a combined preparation for simultaneous, separate or sequential use, in particular in the treatment of cancer;
a product or kit containing a) a conjugated Dbait molecule or hairpin nucleic acid molecule as disclosed below, b) an endosomolytic agent as described below, and optionally c) a DNA-damaging anti-tumoral agent, as a combined preparation for simultaneous, separate or sequential use, in particular in the treatment of cancer;
a combined preparation which comprises a) a conjugated Dbait molecule or hairpin nucleic acid molecule as disclosed below, b) an endosomolytic agent as described below, and optionally c) a DNA-damaging anti-tumoral agent for simultaneous, separate or sequential use, in particular in the treatment of cancer;
a pharmaceutical composition comprising a conjugated Dbait molecule or hairpin nucleic acid molecule as disclosed below, for the use in the treatment of cancer in combination with radiotherapy and/or a DNA-damaging anti-tumoral agent;
a pharmaceutical composition comprising a) a conjugated Dbait molecule or hairpin nucleic acid molecule as disclosed below, and b) an endosomolytic agent as described below, for the use in the treatment of cancer in combination with radiotherapy and/or a DNA-damaging anti-tumoral agent;
a product or kit containing a) a conjugated Dbait molecule or hairpin nucleic acid molecule as disclosed below, and b) an endosomolytic agent as described below, as a combined preparation for simultaneous, separate or sequential use, in particular in the treatment of cancer in combination with radiotherapy and/or a DNA-damaging anti-tumoral agent;
the use of a pharmaceutical composition comprising a conjugated Dbait molecule or hairpin nucleic acid molecule as disclosed below for the manufacture of a medicament for the treatment of cancer in combination with radiotherapy and/or a DNA-damaging anti-tumoral agent or for increasing the efficiency of the treatment of cancer with radiotherapy and/or a DNA-damaging anti-tumoral agent or for enhancing tumor sensitivity to radiotherapy and/or to treatment with a DNA-damaging anti-tumoral agent;
the use of a pharmaceutical composition comprising a conjugated Dbait molecule or hairpin nucleic acid molecule as disclosed below for the manufacture of a medicament for the treatment of cancer in combination with radiotherapy and/or a DNA-damaging anti-tumoral agent and with an endosomolytic agent as disclosed below;
the use of a pharmaceutical composition comprising a) a conjugated Dbait molecule or hairpin nucleic acid molecule as disclosed herein, and b) an endosomolytic agent as described below for the manufacture of a medicament for the treatment of cancer in combination with radiotherapy and/or a DNA-damaging anti-tumoral agent;
the use of a pharmaceutical composition comprising a) a conjugated Dbait molecule or hairpin nucleic acid molecule as disclosed herein, and b) an endosomolytic agent as described below for the manufacture of a medicament for increasing the efficiency of the treatment of cancer with radiotherapy and/or a DNA-damaging anti-tumoral agent or for enhancing tumor sensitivity to radiotherapy and/or to treatment with a DNA-damaging anti-tumoral agent;
the use of a pharmaceutical composition comprising a) a conjugated Dbait molecule or hairpin nucleic acid molecule as disclosed herein, b) an endosomolytic agent as described below, and optionally c) a DNA-damaging anti-tumoral agent and a pharmaceutically acceptable carrier for the manufacture of a medicament for the treatment of cancer;

a method for treating a cancer in a subject in need thereof, comprising administering an effective amount of a pharmaceutical composition comprising a conjugated Dbait molecule or hairpin nucleic acid molecule as disclosed herein, and optionally a DNA-damaging anti-tumoral agent, and a pharmaceutically acceptable carrier;

a method for treating a cancer in a subject in need thereof, comprising administering an effective amount of a pharmaceutical composition comprising a) a conjugated Dbait molecule or hairpin nucleic acid molecule as disclosed herein, b) an endosomolytic agent as described below, and optionally c) a DNA-damaging anti-tumoral agent, and a pharmaceutically acceptable carrier;

a method for treating a cancer in a subject in need thereof, comprising administering an effective amount of a pharmaceutical composition comprising a conjugated Dbait molecule or hairpin nucleic acid molecule as disclosed herein, an effective amount of a pharmaceutical composition comprising an endosomolytic agent as described below and optionally an effective amount of a pharmaceutical composition comprising a DNA-damaging anti-tumoral agent;

a method for treating a cancer in a subject in need thereof, comprising administering an effective amount of a pharmaceutical composition comprising a) a conjugated Dbait molecule or hairpin nucleic acid molecule as disclosed herein and b) an effective amount of a pharmaceutical composition comprising an endosomolytic agent as described below in combination with radiotherapy and/or a DNA-damaging anti-tumoral agent;

a method for increasing the efficiency of a treatment of a cancer with radiotherapy and/or a DNA-damaging anti-tumoral agent or for enhancing tumor sensitivity to radiotherapy and/or to treatment with a DNA-damaging anti-tumoral agent in a subject in need thereof, comprising administering an effective amount of a pharmaceutical composition comprising a) a conjugated Dbait molecule or hairpin nucleic acid molecule as disclosed herein and b) an endosomolytic agent as described below, and a pharmaceutically acceptable carrier; and a method for increasing the efficiency of a treatment of a cancer with radiotherapy and/or a DNA-damaging anti-tumoral agent or for enhancing tumor sensitivity to radiotherapy and/or to treatment with a DNA-damaging anti-tumoral agent in a subject in need thereof, comprising administering an effective amount of a pharmaceutical composition comprising a conjugated Dbait molecule or hairpin nucleic acid molecule as disclosed herein, and an effective amount of a pharmaceutical composition comprising an endosomolytic agent as described below.

The terms "kit", "product" or "combined preparation", as used herein, define especially a "kit of parts" in the sense that the combination partners (a) and (b), and optionally (c), as defined above can be dosed independently or by use of different fixed combinations with distinguished amounts of the combination partners (a) and (b), and optionally (c), i.e., simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b), and optionally (c), to be administered in the combined preparation can be varied. The combination partners (a) and (b), and optionally (c), can be administered by the same route or by different routes.

Within the context of the invention, the term "treatment" denotes curative, symptomatic, and preventive treatment. Pharmaceutical compositions, kits, products and combined preparations of the invention can be used in humans with an existing cancer or tumor, including at early or late stages of progression of the cancer. The pharmaceutical compositions, kits, products and combined preparations of the invention will not necessarily cure the patient who has the cancer but will delay or slow the progression or prevent further progression of the disease, improving thereby the patient's condition. In particular, the pharmaceutical compositions, kits, products and combined preparations of the invention reduce the development of tumors, reduce tumor burden, produce tumor regression in a mammalian host and/or prevent metastasis occurrence and cancer relapse. In treating the cancer, the pharmaceutical composition of the invention is administered in a therapeutically effective amount.

By "effective amount" it is meant the quantity of the pharmaceutical composition of the invention which prevents, removes or reduces the deleterious effects of cancer in mammals, including humans, alone or in combination with the other active ingredients of the pharmaceutical composition, kit, product or combined preparation. It is understood that the administered dose may be adapted by those skilled in the art according to the patient, the pathology, the mode of administration, etc.

Whenever the term "treatment of a cancer" or the like is used within this specification with reference to the pharmaceutical composition of the invention, it refers to: a) a method for treating a cancer, said method comprising administering a pharmaceutical composition of the invention to a subject in need of such treatment; b) the use of a pharmaceutical composition of the invention for the treatment of a cancer; c) the use of a pharmaceutical composition of the invention for the manufacture of a medicament for the treatment of a cancer; and/or d) a pharmaceutical composition of the invention for use in the treatment a cancer.

Dbait Molecules

Dbait molecules have been extensively described in PCT patent applications WO2005/040378, WO2008/034866 and WO2008/084087, the disclosures of which are incorporated herein by reference.

Dbait molecules may be defined by a number of characteristics necessary for their therapeutic activity, such as their minimal length, the presence of at least one free end, and the presence of a double-stranded portion, preferably a double-stranded DNA portion. As will be discussed below, it is important to note that the precise nucleotide sequence of Dbait molecules does not impact their activity. Furthermore, Dbait molecules may contain a modified and/or non-natural backbone.

Preferably, Dbait molecules are of non-human origin (i.e., their nucleotide sequence and/or conformation (e.g., hairpin) does not exist as such in a human cell), most preferably of synthetic origin. As the sequence of the Dbait molecules plays little, if any, role, Dbait molecules have preferably no significant degree of sequence homology or identity to known genes, promoters, enhancers, 5'- or 3'-upstream sequences, exons, introns, and the like. In other words, Dbait molecules have less than 80% or 70%, even less than 60% or 50% sequence identity to any gene in a human genome. Methods of determining sequence identity are well known in the art and include, e.g., BLASTN 2.2.25. By human genome, it is preferably considered for determining the identity percentage the Human Genome Build 37 (reference GRCh37.p2 and alternate assemblies). Dbait molecules do not hybridize, under stringent conditions, with human genomic DNA. Typical stringent conditions are such that they allow the discrimination of fully complementary nucleic acids from partially complementary nucleic acids.

In addition, the sequence of the Dbait molecules is preferably devoid of CpG in order to avoid the well-known toll-like receptor-mediated immunological reactions.

The length of Dbait molecules may be variable, as long as it is sufficient to allow appropriate binding of Ku protein complexes comprising Ku and DNA-PKcs proteins. It has been shown that the length of Dbait molecules must be greater than 20 bp, preferably about 32 bp, to ensure binding to such a Ku complex and allow DNA-PKcs activation. Preferably, Dbait molecules comprise between 20-200 bp, more preferably 24-100 bp, still more preferably 26-100, and most preferably between 32-100 bp. For instance, Dbait molecules comprise between 24-160, 26-150, 28-140, 30-120, or 32-100 bp. By "bp" is intended that the molecule comprise a double stranded portion of the indicated length.

In a particular embodiment, the Dbait molecules having a double-stranded portion of at least 32 bp, or of about 32 bp, comprise the same nucleotide sequence as Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5). Optionally, the Dbait molecules have the same nucleotide composition as Dbait32, Dbait32Ha, Dbait32Hb, Dbait32Hc or Dbait32Hd but their nucleotide sequence is different; then the Dbait molecules comprise one strand of the double-stranded portion with 3 A, 6 C, 12 G and 11 T. Preferably, the sequence of the Dbait molecules does not contain any CpG dinucleotide.

Alternatively, the double-stranded portion comprises at least 16, 18, 20, 22, 24, 26, 28, 30 or 32 consecutive nucleotides of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5). In a more particular embodiment, the double-stranded portion consists of 20, 22, 24, 26, 28, 30 or 32 consecutive nucleotides of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5).

Dbait must have at least one free end, as a mimic of DSB. Said free end may be either a free blunt end or a 5'-/3'-protruding end. The "free end" refers herein to a nucleic acid molecule, in particular a double-stranded nucleic acid portion, having both a 5' end and a 3' end or having either a 3' end or a 5' end. Optionally, one of the 5' and 3' end can be used to conjugate the Dbait molecule or can be linked to a blocking group, for instance a 3'-3' nucleotide linkage.

In a particular embodiment, they contain two free ends and can be linear. Accordingly, the Dbait molecules may also be double-stranded molecules with two free ends and having the nucleotide sequence of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5).

In another particular embodiment, they contain only one free end. Preferably, the Dbait molecules are made of hairpin nucleic acids with a double-stranded DNA stem and a loop. The loop can be a nucleic acid or other chemical groups known by a skilled person or a mixture thereof. A nucleotide linker may include from 2 to 10 nucleotides, preferably 3, 4 or 5 nucleotides. Non-nucleotide linkers non-exhaustively include abasic nucleotides, polyethers, polyamines, polyamides, peptides, carbohydrates, lipids, polyhydrorarbons, or other polymeric compounds (e.g., oligoethylene glycols such as those having between 2 and 10 ethylene glycol units, preferably 4, 5, 6, 7 or 8 ethylene glycol units). A preferred linker is selected from the group consisting of hexaethyleneglycol, tetradeoxythymidylate (T4) and other linkers such as 2,19-bis(phosphor)-8-hydraza-1-hydroxy-4-oxa-9-oxo-nonadecane. Accordingly, in a particular embodiment, the Dbait molecules can be hairpin molecules having a double-stranded portion or stem comprising at least 16, 18, 20, 22, 24, 26, 28, 30 or 32 consecutive nucleotides of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5) and a loop being a hexaethyleneglycol linker, a tetradeoxythymidylate linker (T4) or 2,19-bis(phosphor)-8-hydraza-1-hydroxy-4-oxa-9-oxo-nonadecane. In a more particular embodiment, those Dbait molecules can have a double-stranded portion consisting of 20, 22, 24, 26, 28, 30 or 32 consecutive nucleotides of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5).

Dbait molecules preferably comprise a 2'-deoxynucleotide backbone, and optionally comprise one or several (2, 3, 4, 5 or 6) modified nucleotides and/or nucleobases other than adenine, cytosine, guanine and thymine. Accordingly, the Dbait molecules are essentially a DNA structure. In particular, the double-stranded portion or stem of the Dbait molecules is made of deoxyribonucleotides.

Preferred Dbait molecules comprise one or several chemically modified nucleotide(s) or group(s) at the end of one or each strand, in particular in order to protect them from degradation. In a particular preferred embodiment, the free end(s) of the Dbait molecules is(are) protected by one, two or three modified phosphodiester backbones at the end of one or each strand. Preferred chemical groups, in particular the modified phosphodiester backbone, comprise phosphorothioates. Alternatively, preferred Dbait have 3'-3' nucleotide linkage, or nucleotides with methylphosphonate backbones. Other modified backbones are well known in the art and comprise phosphoramidates, morpholino nucleic acid, 2'-0,4'-C methylene/ethylene bridged locked nucleic acid, peptide nucleic acid (PNA), and short chain alkyl or cycloalkyl intersugar linkages or short chain heteroatomic or heterocyclic intrasugar linkages of variable length, or any modified nucleotides known by a skilled person. In a first preferred embodiment, the Dbait molecules have the free end(s) protected by one, two or three modified phosphodiester backbones at the end of one or each strand, more preferably by three modified phosphodiester backbones (in particular phosphorothioate or methylphosphonate) at least at the 3'end, but still more preferably at both the 5' and 3' ends.

In a most preferred embodiment, the Dbait molecule is a hairpin nucleic acid molecule comprising a DNA double-stranded portion or stem of 32 bp (e.g., with a sequence selected from the group consisting of SEQ ID NOS: 1-5, in particular SEQ ID NO: 4) and a loop linking the two strands of the DNA double-stranded portion or stem comprising or consisting of a linker selected from the group consisting of hexaethyleneglycol, tetradeoxythymidylate (T4) and 2,19-bis(phosphor)-8-hydraza-1-hydroxy-4-oxa-9-oxo-nonadecane, the free ends of the DNA double-stranded portion or stem (i.e., at the opposite of the loop) having three modified phosphodiester backbones (in particular phosphorothioate internucleotidic links).

Said Dbait molecules are made by chemical synthesis, semi-biosynthesis or biosynthesis, any method of amplification, followed by any extraction and preparation methods and any chemical modification. Linkers are provided so as to be incorporable by standard nucleic acid chemical synthesis.

More preferably, Dbait molecules are manufactured by specially designed convergent synthesis: two complementary strands are prepared by standard nucleic acid chemical synthesis with the incorporation of an appropriate linker precursor, and after their purification, they are covalently coupled together.

Conjugated Dbait Molecules

The present invention concerns Dbait molecules conjugated to molecules facilitating endocytosis or cellular uptake.

In particular, the molecules may be lipophilic molecules such as cholesterol, single or double chain fatty acids, or ligands which target cell receptors, enabling receptor-mediated endocytosis, such as folic acid and folate derivatives or transferrin (Goldstein et al., Ann. Rev. Cell Biol., 1985, 1:1-39; Leamon & Lowe, Proc Natl Acad Sci USA, 1991, 88: 5572-5576). Fatty acids may be saturated or unsaturated and be in $C_4$-$C_{28}$, preferably in $C_{14}$-$C_{22}$, still more preferably in $C_{18}$ such as oleic acid or stearic acid. In particular, fatty acids may be octadecyl or dioleoyl. Fatty acids may be found in double chain form linked with an appropriate linker such as a glycerol, a phosphatidylcholine or ethanolamine and the like or linked together by the linkers used to attach to the Dbait molecule. As used herein, the term "folate" refers to folate and folate derivatives, including pteroic acid derivatives and analogs. The analogs and derivatives of folic acid suitable for use in the present invention include, but are not limited to, antifolates, dihydrofolates, tetrahydrofolates, folinic acid, pteropolyglutamic acid, 1-deza, 3-deaza, 5-deaza, 8-deaza, 10-deaza, 1,5-deaza, 5,10-dideaza, 8,10-dideaza, and 5,8-dideaza folates, antifolates, and pteroic acid derivatives. Additional folate analogs are described in US2004/242582. The molecule facilitating endocytosis may be tocopherol, a sugar such as galactose and mannose and their oligosaccharides, a peptide such as RGD and bombesin, or a protein such as integrin. Accordingly, the molecule facilitating endocytosis may be selected from the group consisting of single or double chain fatty acids, folates and cholesterol. More preferably, the molecule facilitating endocytosis is selected from the group consisting of dioleoyl, octadecyl, folic acid, and cholesterol. In a most preferred embodiment, the Dbait molecule is conjugated to a cholesterol.

The molecules facilitating endocytosis are conjugated to the Dbait molecules, preferably through a linker. Any linker known in the art may be used to covalently attach the molecule facilitating endocytosis to the Dbait molecules. For instance, WO09/126933 provides a broad review of convenient linkers pages 38-45. The linker can be, non-exhaustively, an aliphatic chain, polyether, polyamine, polyamide, peptide, carbohydrate, lipid, polyhydrocarbon, or other polymeric compound (e.g., oligoethylene glycols such as those having between 2 and 10 ethylene glycol units, preferably 3, 4, 5, 6, 7 or 8 ethylene glycol units, still more preferably 6 ethylene glycol units), as well as incorporating any bonds that may be broken down chemically or enzymatically, such as a disulfide linkage, a protected disulfide linkage, an acid labile linkage (e.g., a hydrazone linkage), an ester linkage, an ortho ester linkage, a phosphonannde linkage, a biocleavable peptide linkage, an azo linkage or an aldehyde linkage. Such cleavable linkers are detailed in WO2007/040469, pages 12-14, and WO2008/022309, pages 22-28.

In a particular embodiment, the Dbait molecule can be linked to one molecule facilitating endocytosis. Alternatively, several molecules facilitating endocytosis (e.g., two, three or four) can be attached to one Dbait molecule.

In a specific embodiment, the linker between the molecule facilitating endocytosis, in particular cholesterol, and the Dbait molecule is CO—NH—$(CH_2$—$CH_2$—$O)_n$, wherein n is an integer from 1 to 10, preferably n being selected from the group consisting of 3, 4, 5 and 6. In a very particular embodiment, the linker is CO—N—$(CH_2$—$CH_2$—$O)_4$ (carboxamido triethylene glycol). The linker can be linked to the Dbait molecules at any convenient position which does not modify the activity of the Dbait molecules. In particular, the linker can be linked at the 5' end, at the 3' end or in the loop when the Dbait molecule is a hairpin. However, in the case of a hairpin Dbait molecule, the inventors surprisingly found that cholesterol linked to the Dbait molecule through a linker at its 5' end is more efficient than cholesterol linked to the Dbait molecule through a linker at the loop. Therefore, in a preferred embodiment, the contemplated conjugated Dbait molecule is a Dbait molecule having a hairpin structure and being conjugated to the molecule facilitating endocytosis, preferably through a linker, at its 5' end.

In another specific embodiment, the linker between the molecule facilitating endocytosis, in particular cholesterol, and the Dbait molecule is dialkyl-disulfide (e.g., $(CH_2)_p$—S—S—$(CH_2)_q$ with p and q being integer from 1 to 10, preferably from 3 to 8, for instance 6).

In a most preferred embodiment, the conjugated Dbait molecule is a hairpin nucleic acid molecule comprising a DNA double-stranded portion or stem of 32 bp (e.g., with a sequence selected from the group consisting of SEQ ID NOS: 1-5, in particular SEQ ID NO: 4) and a loop linking the two strands of the DNA double-stranded portion or stem comprising or consisting of a linker selected from the group consisting of hexaethyleneglycol, tetradeoxythymidylate (T4) and 2,19-bis(phosphor)-8-hydraza-1-hydroxy-4-oxa-9-oxo-nonadecane, the free ends of the DNA double-stranded portion or stem (i.e., at the opposite of the loop) having three modified phosphodiester backbones (in particular phosphorothioate internucleotidic links) and said Dbait molecule being conjugated to a cholesterol at its 5' end, preferably through a linker (e.g., carboxamido oligoethylene glycol, preferably carboxamido triethylene glycol).

The conjugated Dbait molecule or hairpin nucleic acid molecule can also be described by the following formulae:

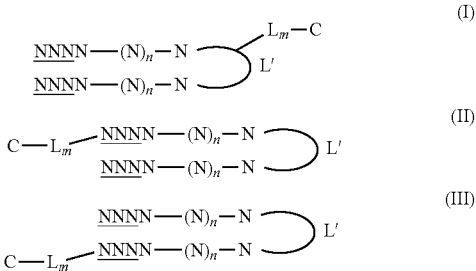

wherein N is a nucleotide, n is an integer greater than 14, the underlined N refers to a nucleotide having or not having a modified phosphodiester backbone, L' is a linker, C is a molecule facilitating endocytosis, L is a linker, and m is an integer being 0 or 1. Preferably, the underlined N refers to a nucleotide having a modified phosphodiester backbone. In Formulae (II) and (III), C-$L_m$ is respectively linked to the 5' end or the 3' end of the nucleotide. In formula (I-III), C-$L_m$ is preferably linked to L' through a disulfide bond (S—S).

In preferred embodiments, the molecule of formula (I), (II) or (III) has one or several of the following features:
- N is a deoxynucleotide, preferably selected from the group consisting of A (adenine), C (cytosine), T (thymine) and G (guanine) and selected so as to avoid occurrence of a CpG dinucleotide and to have less than 80% or 70%, even less than 60% or 50% sequence identity to any gene in a human genome; and/or
- n is an integer from 15 to 195, preferably from 19-95, more preferably from 21 to 95, and still more preferably from 27 to 95. In a particularly preferred embodiment, n is 27; and/or
- the underlined N refers to a nucleotide having a phosphorothioate or methylphosphonate backbone, more preferably a phosphorothioate backbone; and/or
- the linker L' is selected from the group consisting of hexaethyleneglycol, tetradeoxythymidylate (T4) and 2,19-bis(phosphor)-8-hydraza-1-hydroxy-4-oxa-9-oxo-nonadecane; and/or
- m is 1 and L is a carboxamido oligoethyleneglycol, more preferably carboxamido triethylene glycol; and/or
- C is selected from the group consisting of a cholesterol, single or double chain fatty acids such as oleic acid or stearic acid, ligands (including peptides, proteins, and aptamers), which targets cell receptors such as folate, and transferrin, preferably is a cholesterol, octadecyl, dioleoyl or folate, and more preferably is a cholesterol.

Preferably, C-$L_m$ is a triethyleneglycol linker (10-O-[1-propyl-3-N-carbamoylcholesteryl]-triethyleneglycol radical).

In a preferred embodiment, the conjugated Dbait molecule or hairpin nucleic acid molecule has the following formula:

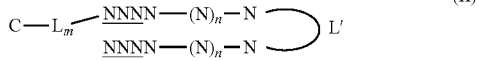
(II)

with the same definition as formulae (I), (II) and (III) for N, underlined N, n, L, L', C and m.

In a preferred embodiment, NNNN—$(N)_r$—N comprises at least 16, 18, 20, 22, 24, 26, 28, 30 or 32 consecutive nucleotides of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5) or consists of 20, 22, 24, 26, 28, 30 or 32 consecutive nucleotides of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5). In a particular embodiment, NNNN—$(N)_r$—N comprises or consists of Dbait32 (SEQ ID NO: 1), Dbait32Ha (SEQ ID NO: 2), Dbait32Hb (SEQ ID NO: 3), Dbait32Hc (SEQ ID NO: 4) or Dbait32Hd (SEQ ID NO: 5), more preferably Dbait32Hc (SEQ ID NO: 4).

Accordingly, the conjugated Dbait molecule or hairpin nucleic acid molecule may be selected from the group consisting of:

with NNNN—$(N)_n$—N being SEQ ID NO: 1

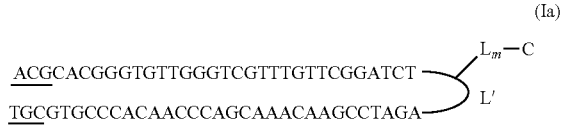
(Ia)

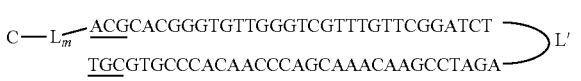
(IIa)

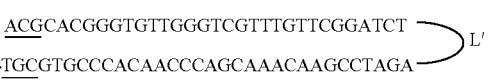
(IIIa)

with NNNN—$(N)_n$—N being SEQ ID NO: 2

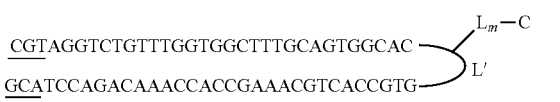
(Ib)

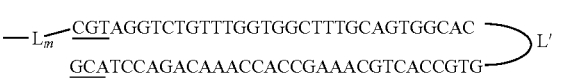
(IIb)

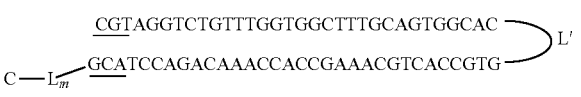
(IIIb)

with NNNN—$(N)_n$—N being SEQ ID NO: 3

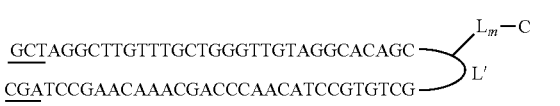
(Ic)

(IIc)

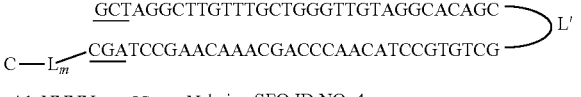
(IIIc)

with NNNN—$(N)_n$—N being SEQ ID NO: 4

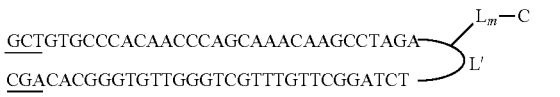
(Id)

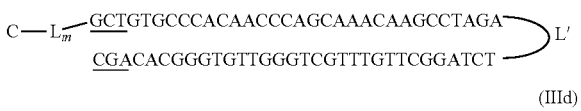
(IId)

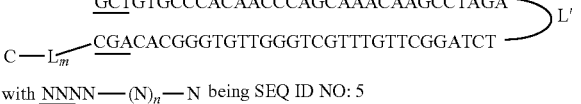
(IIId)

with NNNN—$(N)_n$—N being SEQ ID NO: 5

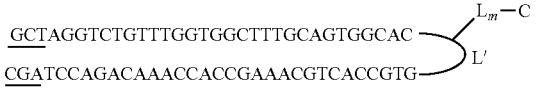
(Ie)

(IIe)

(IIIe)

with the same definition as formulae (I), (II) and (III) for L, L', C and m.

In preferred embodiments, the molecule of formulae (Ia), (IIa), (IIIa), (Ib), (IIb), (IIIb), (Ic), (IIc), (IIIc), (Id), (IId), (IIId), (Ie), (IIe) and (IIIe), preferably formulae (II), (IIa), (IIb), (IIc), (IId) and (IIe), has one or several of the following features:

the underlined nucleotide refers to a nucleotide having or not having a phosphorothioate or methylphosphonate backbone, more preferably a nucleotide having a phosphorothioate or methylphosphonate backbone, still more preferably a nucleotide having a phosphorothioate backbone; and/or the linker L' is selected from the group consisting of hexaethyleneglycol, tetradeoxythymidylate (T4) and 2,19-bis(phosphor)-8-hydraza-1-hydroxy-4-oxa-9-oxo-nonadecane; and/or m is 1 and L is a carboxamido oligoethylene glycol, more preferably carboxamido triethylene glycol; and/or C is selected from the group consisting of a cholesterol, single or double chain fatty acids such as oleic acid or stearic acid, ligands (including peptides, proteins, and aptamers) which targets cell receptors such as folate, and transferrin, and preferably is a cholesterol, octadecyl, dioleoyl or folate, more preferably a cholesterol.

Preferably, C-$L_m$ is a triethyleneglycol linker (10-O-[1-propyl-3-N-carbamoylcholesteryl]-triethyleneglycol radical).

In a specific embodiment of the Dbait molecules or hairpin nucleic acid molecules of formulae (I), (II), (III), (Ia), (IIa), (IIIa), (Ib), (IIb), (IIIb), (Ic), (IIc), (IIIc), (Id), (IId), (IIId), (Ie), (IIe) and (IIIe), preferably formulae (II), (IIa), (IIb), (IIc), (IId) and (IIe), L' is preferably selected from the group consisting of hexaethyleneglycol, tetradeoxythymidylate (T4) and 2,19-bis(phosphor)-8-hydraza-1-hydroxy-4-oxa-9-oxo-nonadecane.

In a specific embodiment of the Dbait molecules or hairpin nucleic acid molecules of formulae (I), (II), (III), (Ia), (IIa), (IIIa), (Ib), (IIb), (IIIb), (Ic), (IIc), (IIIc), (Id), (IId), (IIId), (Ie), (IIe) and (IIIe), preferably formulae (II), (IIa), (IIb), (IIc), (IId) and (IIe), with C being cholesterol, C-$L_m$ is the radical

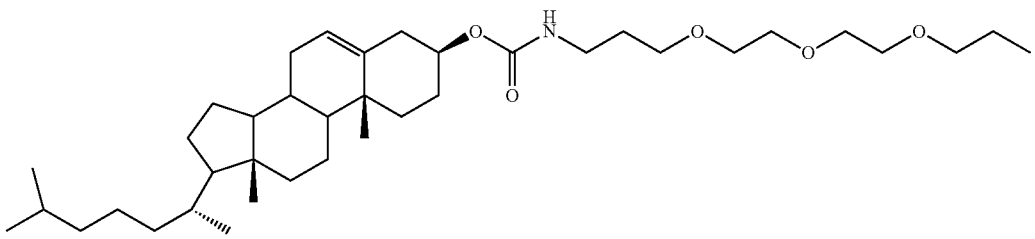 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

In a preferred embodiment, the conjugated Dbait molecule or hairpin nucleic acid molecule is selected from the group consisting of (II), (IIa), (IIb), (IIc), (IId), and (IIe), wherein C-$L_m$ is the radical

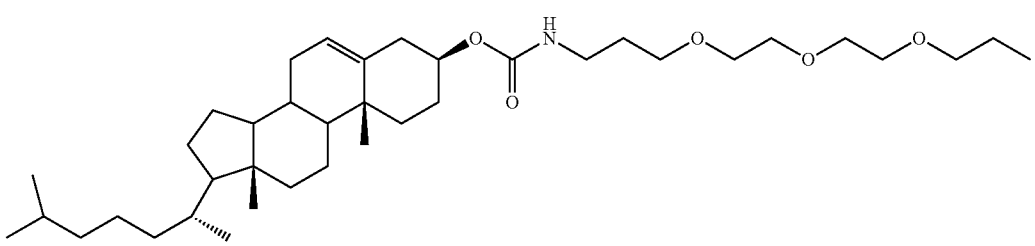 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

and wherein L' is preferably selected from the group consisting of hexaethyleneglycol, tetradeoxythymidylate (T4) and 2,19-bis(phosphor)-8-hydraza-1-hydroxy-4-oxa-9-oxo-nonadecane, more preferably 2,19-bis(phosphor)-8-hydraza-1-hydroxy-4-oxa-9-oxo-nonadecane.

In a very specific embodiment, the Dbait molecule or hairpin nucleic acid molecule has the following formula:

(IId)

wherein $C-L_m$ is the radical

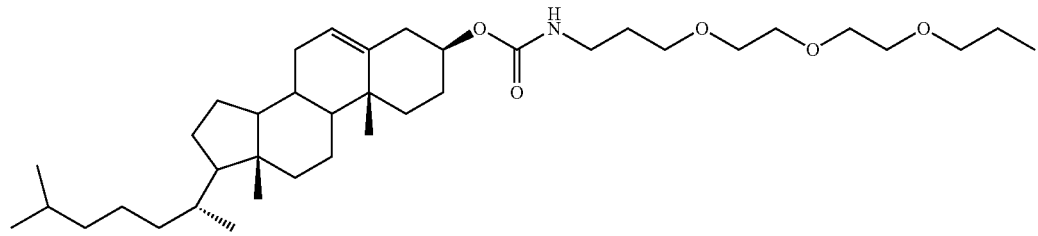

wherein L' is 2,19-bis(phosphor)-8-hydraza-1-hydroxy-4-oxa-9-oxo-nonadecane and wherein the underlined nucleotides have a phosphorothioate backbone. Accordingly, the molecule has the following structure and it is referred thereto in the Example section as "coDbait".

5' end and 3 phosphorothioate internucleotide linkages at each of the 5' and the 3' ends. In solution, the molecule forms an intra-molecular hairpin 32-bp double helix. This double-stranded (ds) DNA structure is essential for its biological activity, and is the active pharmaceutical ingredient (API).

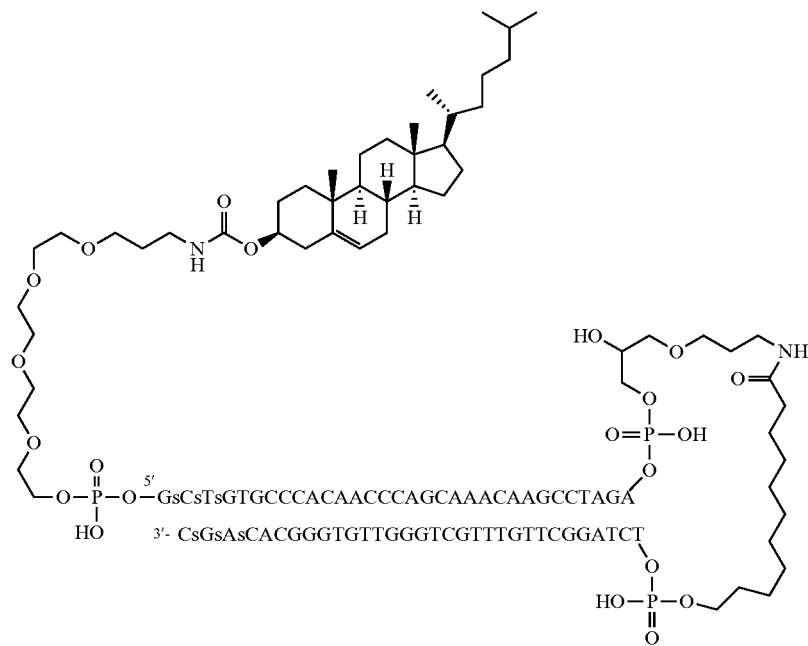

One of the cholesterol-Dbait conjugates, named DT01, is a 64-nt oligodeoxyribonucleotide consisting of two 32-nt strands of complementary sequences connected through a 1,19-bis(phospho)-8-hydraza-2-hydroxy-4-oxa-9-oxo-nonadecane linker, with a cholesterol tetraethyleneglycol at the 5' end and 3 phosphorothioate internucleotide linkages at Molecular formula of the sodium salt: $C_{678}H_{820}N_{244}Na_{65}O_{392}P_{65}S_6$; molecular weight of the sodium salt: 22359.2 Da; molecular weight of the free acid: 20931.4 Da. The molecule can also be represented as follows:

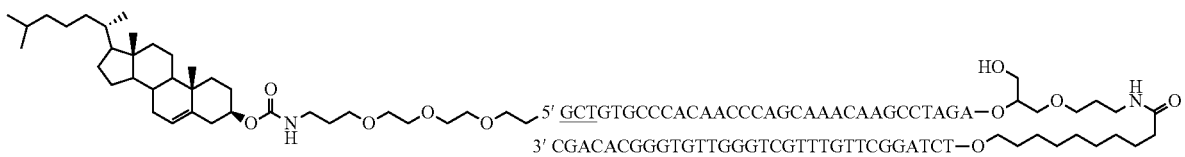

A very surprising aspect of the present invention for the molecule of formula (II), (IIa), (IIb), (IIc), (IId) or (IIe) is that, although the activity of Dbait molecules needs the presence of at least one free end, the molecules facilitating endocytosis linked to the 5' end do not decrease the activity.

Accordingly, the present invention also relates to a conjugated Dbait molecule as disclosed above, a pharmaceutical composition comprising it and optionally a pharmaceutically acceptable carrier, a conjugated Dbait molecule as disclosed above for use in the treatment of cancer, alone or in combination with radiotherapy and/or chemotherapy of a DNA-damaging antitumoral agent, a method for treating cancer comprising administering a therapeutically effective amount of a conjugated Dbait molecule as disclosed above, and the use of a conjugated Dbait molecule as disclosed above for preparing a medicament for treating cancer, as detailed below.

Endosomolytic Agent

Conjugated Dbait molecules or hairpin nucleic acid molecules are preferably used here in combination with an endosomolytic agent (e.g., chloroquine, fusogenic lipids, peptides, etc.). Indeed, treatment by an endosomolytic agent facilitates the release of conjugated Dbait molecules from endosomes. In addition, this particular combination allows the obtention of further surprising effects, including exceptional results with low toxicity in vivo as well as retarded and sustained Dbait-mediated activity.

In particular, the endosomolytic agents are capable of effecting the lysis of the endosome in response to a change in pH, and an encapsulating, or packaging, component capable of packaging a therapeutic agent to be delivered to cellular or subcellular components. Endosomolytic substances include, but are not limited to, quinoline compounds, especially 4-aminoquinoline and 2-phenylquinoline compounds and amino, thio, phenyl, alkyl, vinyl and halogen derivatives thereof, fusogenic lipids, peptides or proteins.

In a preferred embodiment, the endosomolytic agent is a small molecule. The basic endosomolytic agent may be selected from the group consisting of quinine, chloroquine, hydroxychloroquines, amodiaquins (camoquines), amopyroquines, primaquines, mefloquines, nivaquines, halofantrines, quinone imines and a combination thereof. Preferred endosomolytic agents are quinoline endosomolytic agents including, but not limited to, the compounds listed below with their chemical names: 7-chloro-4-(4-diethylamino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline); 4-(4-diethyl-amino-1-butyl amino)quinoline; 7-hydroxy-4-(4-diethylamino-1-butylamino)quinoline; 7-chloro-4-(1-carboxy-4-diethylamino-1-butylamino) quinoline; 7-fluoro-4-(1-carboxy-4-diethyl-amino-1-butylamino)quinoline; 4-(1-carboxy-4-diethylamino-1-butylamino) quinoline; 7-hydroxy-4-(1-carboxy-4-diethylamino-1-butylamino)quinoline; 7-chloro-4-(1-carboxy-4-diethylamino-1-methylbutylamino)quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethyl-amino-1-methylbutylamino)quinoline; 7-fluoro-4-(4-ethyl-(2-hydroxyethyl)-amino-1-methylbutylamino)quinoline; 4-(4-ethyl-(2-hydroxy-ethyl)-amino-1-methylbutylamino) quinoline; 7-hydroxy-4-(4-ethyl-(2-hydroxyethyl)-amino-1-methylbutylamino) quinoline; hydroxychloroquine phosphate; 7-chloro-4-(4-ethyl-(2-hydroxyethyl)-amino-1-butylamino)quinoline (desmethylhydroxychloroquine); 7-fluoro-4-(4-ethyl-(2-hydroxyethyl)-amino-1-butylamino) quinoline; 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino) quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino)quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino)quinoline; 8-[(4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha; alpha'-bis(2-methyl-1-pyrrolidinyl)-2,5-xylidinoquinoline; 4-[(4-diethyl-amino)-1-methylbutyl-amino]-6-methoxyquinoline; 3-fluoro-4-(4-hydroxy-alpha; alpha'-bis (2-methyl-1-pyrrolidinyl)-2,5-xylidinoquinoline; 4-[(4-diethylamino)-1-methylbutyl-amino]-6-methoxyquinoline; 4-(4-hydroxy-alpha; alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. Other agents are disclosed in Naisbitt et al. (1997, *J Pharmacol Exp Therapy* 280:884-893) and in U.S. Pat. No. 5,736,557. In a more preferred embodiment, the endosomolytic agent may be selected from the group consisting of chloroquine, hydroxychloroquine, desmethylchloroquine, hydroxychloroquine phosphate, and desmethyl-hydroxychloroquine, and is preferably chloroquine or hydroxychloroquine, more preferably chloroquine.

In another embodiment, the endosomolytic agent is a fusogenic lipid, peptide or protein. Indeed, numerous fusogenic lipids, peptides or proteins are known in the art. For instance, fusogenic lipids, peptides or proteins are those disclosed in the following patent applications: WO10057160, US2007/0293449, US2006/0051405, WO10053489, and WO09126933. In particular, WO09/126933 provides fusogenic lipids, peptides and proteins at pages 23-29.

The inventors demonstrated the high antitumoral therapeutic efficiency of the combination of a conjugated Dbait molecule with chloroquine, whereas they observed that the same amount of chloroquine alone or in combination with irradiation did not show any anti-tumoral activity.

Accordingly, the present invention concerns a pharmaceutical composition comprising a conjugated Dbait molecule or hairpin nucleic acid molecule of the invention and an endosomolytic agent, more particularly for use in the treatment of cancer. The present invention also concerns a product comprising a conjugated Dbait molecule or hairpin nucleic acid molecule of the invention and an endosomolytic agent as a combined preparation for simultaneous, separate or sequential use, more particularly for use in the treatment of cancer. Preferably, the endosomolytic agent is selected from the group consisting of chloroquine or hydroxychloroquine, and still more preferably is chloroquine. Preferably, the conjugated Dbait molecule or hairpin nucleic acid molecule of the invention is any particular conjugated Dbait molecule as described above. In one embodiment, the Dbait molecule or hairpin nucleic acid molecule of the invention is covalently linked to an endosomolytic agent, preferably chloroquine or hydroxychloroquine, and still more preferably is chloroquine, in particular as disclosed in WO2007/040469. In another preferred embodiment, the endosomolytic agent, preferably chloroquine, is not conjugated (i.e., not covalently linked) to the conjugated Dbait molecule or hairpin nucleic acid molecule of the invention.

The pharmaceutical compositions contemplated herein may include a pharmaceutically acceptable carrier in addition to the active ingredient(s). The term "pharmaceutically acceptable carrier" is meant to encompass any carrier (e.g., support, substance, solvent, etc.) which does not interfere with the effectiveness of the biological activity of the active ingredient(s) and is not toxic to the host to which it is administered. For example, for parenteral administration, the active compound(s) may be formulated in a unit dosage form for injection in vehicles such as saline, dextrose solution, serum albumin and Ringer's solution.

The pharmaceutical compositions can be formulated as solutions in pharmaceutically compatible solvents or as emulsions, suspensions or dispersions in suitable pharmaceutical solvents or vehicles, or as pills, tablets or capsules that contain solid vehicles in a way known in the art. Formulations of the present invention suitable for oral administration may be in the form of discrete units such as capsules, sachets, tablets or lozenges, each containing a predetermined amount of the active ingredient; in the form of a powder or granules; in the form of a solution or a suspension in an aqueous or non-aqueous liquid; or in the form of an oil-in-water or water-in-oil emulsion. Formulations suitable for parenteral administration conveniently comprise a sterile oily or aqueous preparation of the active ingredient which is preferably isotonic with the blood of the recipient. Every such formulation can also contain other pharmaceutically compatible and nontoxic auxiliary agents, such as stabilizers, antioxidants, binders, dyes, emulsifiers or flavouring substances. The formulations of the present invention comprise an active ingredient in association with a pharmaceutically acceptable carrier and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or by oral dosage by the digestive tract. Methods for the safe and effective administration of most of these chemotherapeutic agents are known to those skilled in the art. In addition, their administration is described in the standard literature.

The pharmaceutical composition of the invention is not a liposomal composition. In particular, the conjugated Dbait molecule of the product of the invention is not formulated in a liposomal composition.

In particular, the present invention also relates to a product, kit or combined preparation comprising (a) one or more unit dosage forms of a Dbait molecule or hairpin nucleic acid molecule as disclosed above, (b) one or more unit dosage forms of an endosomolytic agent as disclosed above, and optionally (c) one or more unit dosage forms of a DNA-damaging anti-tumoral agent as disclosed below.

DNA Damaging Treatment

In addition to the conjugated Dbait molecules and the endosomolytic agent, the treatment may also further comprise an antitumoral treatment, preferably a treatment by a DNA-damaging agent or radiotherapy. The DNA-damaging treatment can be radiotherapy or chemotherapy with a DNA-damaging antitumoral agent, or a combination thereof.

DNA strand breakage can be achieved by ionized radiation (radiotherapy). Radiotherapy includes, but is not limited to, γ-rays, X-rays, and/or the directed delivery of radioisotopes to tumor cells. Other radiotherapies include microwaves and UV irradiation. Other approaches to radiation therapy are also contemplated in the present invention.

The DNA-damaging antitumoral agent is preferably selected from the group consisting of an inhibitor of topoisomerases I or II, a DNA crosslinker, a DNA alkylating agent, an anti-metabolic agent and inhibitors of the mitotic spindles.

Inhibitors of topoisomerases I and/or II include, but are not limited to, etoposide, topotecan, camptothecin, irinotecan, amsacrine, intoplicine, anthracyclines such as doxorubicine, epirubicine, daunorubicine, idanrubicine and mitoxantrone. Inhibitors of topoisomerases I and II include, but are not limited to, intoplecin.

DNA crosslinkers include, but are not limited to, cisplatin, carboplatin and oxaliplatin.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatine, 5-Fluorouracil, Gemcitabine and Capecitabine.

The DNA-damaging anti-tumoral agent can be an alkylating agent including, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CYTOXAN(R)), Ifosfamide, Melphalan, Chlorambucil, Pipobroman, Triethylenemelamine, Triethylenethiophosphoramine, Busulfan, Carmustine, Lomustine, Fotemustine, Cisplatin, Carboplatin, Oxaliplatin, Thiotepa, Streptozocin, Dacarbazine, and Temozolomide.

Inhibitors of the mitotic spindles include, but are not limited to, paclitaxel, docetaxel, vinorelbine, larotaxel (also called XRP9881; Sanofi-Aventis), XRP6258 (Sanofi-Aventis), BMS-184476 (Bristol-Myers-Squibb), BMS-188797 (Bristol-Myers-Squibb), BMS-275183 (Bristol-Myers-Squibb), ortataxel (also called IDN 5109, BAY 59-8862 or SB-T-101131; Bristol-Myers-Squibb), RPR 109881A (Bristol-Myers-Squibb), RPR 116258 (Bristol-Myers-Squibb), NBT-287 (TAPESTRY), PG-paclitaxel (also called CT-2103, PPX, paclitaxel poliglumex, paclitaxel polyglutamate or XYOTAX), ABRAXANE (also called Nab-Paclitaxel; ABRAXIS BIOSCIENCE), Tesetaxel (also called DJ-927), IDN 5390 (INDENA), Taxoprexin (also called docosahexanoic acid-paclitaxel; PROTARGA), DHA-paclitaxel (also called TAXOPREXIN), and MAC-321 (WYETH). Also see the review of Hennenfent & Govindan (2006, *Annals of Oncology*, 17, 735-749).

Cancers or Tumors to be Treated

The pharmaceutical compositions and the products, kits or combined preparations described in the invention can be used for treating cancer in a subject.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome-positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, head and neck cancer, gastric cancer, germ cell tumor, pediatric sarcoma, sinonasal natural killer, multiple myeloma, acute myelogenous leukemia (AML), chronic lymphocytic leukemia, mastocytosis and any symptoms associated with mastocytosis.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblast leukemia, myelocytic leukemia, myeloid granulocytic leukemia, myelomonocytic leukemia, Naegeli's leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome-positive acute lymphoblastic leukemia (Ph+ALL).

Various cancers are also encompassed by the scope of the invention, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins's lymphoma, non-Hodgkin's lymphoma, hairy cell lymphoma, histiocytic lymphoma, and Burkitt's lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, head and neck cancer, retinoblastoma, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasm, plasma cell neoplasm, myelodysplastic syndromes, neuroblastoma, testicular germ cell tumor, intraocular melanoma, myelodysplastic syndromes; myelodysplastic/myeloproliferative diseases, and synovial sarcoma. In addition, disorders include urticaria pigmentosa; mastocytoses such as diffuse cutaneous mastocytosis, solitary mastocytoma in human, as well as dog mastocytoma, and some rare subtypes like bullous, erythrodermic and teleangiectatic mastocytosis; mastocytosis with an associated hematological disorder, such as a myeloproliferative or myelodysplastic syndrome, or acute leukemia; myeloproliferative disorder associated with mastocytosis; and mast cell leukemia, in addition to other cancers. Other cancers are also included within the scope of disorders including, but not limited to, the following: carcinoma, including that of the bladder, urothelial carcinoma, breast, colon, kidney, liver, lung, ovary, pancreas, stomach, cervix, thyroid, testis, particularly testicular seminomas, and skin, including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

In a preferred embodiment of the present invention, the cancer is a solid tumor. The term "solid tumor" especially means breast cancer, ovarian cancer, cancer of the colon and generally the GI (gastrointestinal) tract, cervical cancer, lung cancer, in particular small-cell lung cancer and non-small-cell lung cancer, head and neck cancer, bladder cancer, cancer of the prostate or Kaposi's sarcoma.

The pharmaceutical compositions and the products, kits or combined preparations described in the invention may be useful for inhibiting the growth of solid tumors, decreasing the tumor volume, and preventing the metastatic spread of tumors and the growth or development of micrometastases. The pharmaceutical compositions and the products, kits or combined preparations described in the invention are in particular suitable for the treatment of poor-prognosis patients or of radio- or chemo-resistant tumors.

The inventors tested a high number of different tumoral types for each tumor (including melanomas, glioblastomas, and carcinomas) from cell lines and patients' biopsies. More than 80% of them responded well to the treatment. In particular, efficiency has been observed for the following tumoral types: melanoma, glioblastoma, breast cancer, colon cancer, gastrointestinal cancer, liver cancer and head and neck cancer.

In a preferred embodiment, the cancer can be selected from melanoma, glioblastoma, breast cancer, colon cancer, gastrointestinal cancer, liver cancer and head and neck cancer.

Regimen, Dosages and Administration Routes

The effective dosage of each of the combination partners employed in the combined preparation of the invention may vary depending on the particular compound or pharmaceutical composition employed, the mode of administration, the condition being treated, and the severity of the condition being treated. Thus, the dosage regimen of the combined preparation of the invention is selected in accordance with a variety of factors including the route of administration and the patient status. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

The endosomolytic agent and the conjugated Dbait molecules may be administered by the same route or by two distinct routes. The administration route for the endosomolytic agent, preferably chloroquine or hydroxychloroquine, more preferably chloroquine, and/or the conjugated Dbait molecules may be oral, parenteral, intravenous, intratumoral, subcutaneous, intracranial, intra-arterial, topical, rectal, transdermal, intradermal, nasal, intramuscular, intraperitoneal, intraosseous, or the like. In a preferred embodiment, the conjugated Dbait molecules are to be administered or injected near the tumoral site(s) to be treated.

In a particular embodiment, the endosomolytic agent, preferably chloroquine or hydroxychloroquine, more preferably chloroquine, is to be administered by an oral route or by an intraperitoneal route, preferably by an oral route, and the conjugated Dbait molecules may be administered by intratumoral injection, by subcutaneous injection, by intraperitoneal injection, by intracranial injection, by intravenous injection, or by an oral route, more preferably by intratumoral, subcutaneous or intravenous injection, still most preferably by a subcutaneous route.

In another particular embodiment, the endosomolytic agent, preferably chloroquine or hydroxychloroquine, more preferably chloroquine, and the conjugated Dbait molecules are to be administered both by intratumoral injection, by subcutaneous injection, by intraperitoneal injection, by intravenous injection, or by an oral route, more preferably by intratumoral, subcutaneous injection or by an oral route, still most preferably by an oral route. When the endosomolytic agent, preferably chloroquine or hydroxychloroquine, more preferably chloroquine, and the conjugated Dbait molecules are co-injected, the higher the amount of the endosomolytic agent, preferably chloroquine, the better the therapeutic effect, within the limit of its toxicity. An advantage of the co-injection or local injection is that there is no need to match the pharmacokinetic profile in plasma. In a very specific embodiment, the endosomolytic agent, preferably chloroquine, is administered by an oral route, and the conjugated Dbait molecules are to be administered by subcutaneous injection. The inventors demonstrate exceptional results with this combination of administration routes, provided a pre-treatment of chloroquine is administered in order to establish a steady-state regimen of chloroquine in the plasma.

The endosomolytic agent, preferably chloroquine or hydroxychloroquine, more preferably chloroquine, is to be administered 2 hours before and/or simultaneously with and/or after cholesterol-conjugated Dbait molecules or hairpin nucleic acid molecules, more preferably 2 hours before the administration of coDbait.

In a first preferred embodiment, the treatment regimen includes a step of pre-treatment of the patient with the endosomolytic agent, preferably chloroquine, before the beginning of the treatment with cholesterol-conjugated Dbait molecules or hairpin nucleic acid molecules. For instance, when the endosomolytic agent is administered near the tumoral site to be treated (e.g., local administration), it can be administered together or at least or about 1, 2, 3, 4 or 5 hours before the administration of conjugated Dbait molecules or hairpin nucleic acid molecules, preferably between about one to three hours before, more preferably about two hours before. Alternatively, when the endosomolytic agent is administered by systemic administration, it can be administered longer before the administration of conjugated Dbait molecules or hairpin nucleic acid molecules and by a longer treatment, preferably during a period of about one to three weeks before the administration of cholesterol-conjugated Dbait molecules or hairpin nucleic acid molecules, more preferably about a period of about two weeks.

Once cholesterol-conjugated Dbait molecules or hairpin nucleic acid molecules are or have been administered, the treatment with the endosomolytic agent can continue as long as the cholesterol-conjugated Dbait molecules or hairpin nucleic acid molecules are to be administered. Alternatively, the treatment with the endosomolytic agent can also end.

When a DNA-damaging antitumoral agent is used in combination with the conjugated Dbait molecule and the endosomolytic agent, the DNA-damaging antitumoral agent and the cholesterol-conjugated Dbait molecules may be administered by the same route or by distinct routes. The administration route for the DNA-damaging antitumoral agent may be oral, parenteral, intravenous, intratumoral, subcutaneous, intracranial, intraarterial, topical, rectal, transdermal, intradermal, nasal, intramuscular, intraosseous, or the like.

In a particular embodiment, the DNA-damaging antitumoral agent and the endosomolytic agent are to be administered by an oral route, simultaneously, separately or sequentially, and the conjugated Dbait molecules may be administered by intratumoral injection, by subcutaneous injection, by intraperitoneal injection, by intravenous injection, or by an oral route, preferably by intratumoral, subcutaneous or intraperitoneal injection or by an oral route, still more preferably by intratumoral or subcutaneous.

In another particular embodiment, the DNA-damaging antitumoral agent is to be administered by an oral route, and the conjugated Dbait molecules and the endosomolytic agent may be administered, simultaneously, separately or sequentially, by intratumoral injection, by subcutaneous injection, by intraperitoneal injection, by intravenous injection, or by an oral route, preferably by intratumoral, subcutaneous or intraperitoneal injection or by an oral route, still more preferably by intratumoral or subcutaneous.

In a further particular embodiment, the endosomolytic agent is to be administered by an oral route, and the conjugated Dbait molecules and the DNA-damaging antitumoral agent may be administered, simultaneously, separately or sequentially, by intratumoral injection, by subcutaneous injection, by intraperitoneal injection, by intravenous injection, or by an oral route, preferably by intratumoral, subcutaneous or intraperitoneal injection or by an oral route, still more preferably by intratumoral or subcutaneous.

In an additional particular embodiment, the DNA-damaging antitumoral agent, the endosomolytic agent and the conjugated Dbait molecules are to be administered, simultaneously, separately or sequentially, by intratumoral injection, by subcutaneous injection, by intraperitoneal injection, by intravenous injection, or by an oral route, preferably by intratumoral, subcutaneous or intraperitoneal injection or by an oral route, still more preferably by intratumoral or subcutaneous injection.

The endosomolytic agent and conjugated Dbait molecules or hairpin nucleic acid molecules are to be administered before and/or simultaneously with and/or after the irradiation and/or the administration of the DNA-damaging antitumoral agent, more preferably before and/or simultaneously with the irradiation and/or the administration of the DNA-damaging antitumoral agent. The irradiation and/or the administration of the DNA-damaging antitumoral agent is performed so that the conjugated Dbait molecules are present in the tumoral cells when the irradiation is applied or when the DNA-damaging antitumoral agent reaches the tumoral cells. A physician, clinician or veterinarian of ordinary skill can determine the regimen based on the active ingredients, their kinetics of availability to target sites or their pharmacokinetic profiles in plasma. Preliminary results indicate that conjugated Dbait molecules stay active during one day. In a first preferred embodiment, the treatment regimen includes a step of pre-treatment of the patient with the endosomolytic agent, preferably chloroquine or hydroxychloroquine, more preferably chloroquine, before the beginning of the treatment with the conjugated Dbait molecules or hairpin nucleic acid molecules. Then, the irradiation is to be applied or the DNA-damaging antitumoral agent is to be administered at the beginning of the treatment with the conjugated Dbait molecules or hairpin nucleic acid molecules or after the treatment with the conjugated Dbait molecules or hairpin nucleic acid molecules. For instance, the irradiation is to be applied or the DNA-damaging antitumoral agent is to be administered 3-24 h after the beginning of the treatment with the conjugated Dbait molecules. The DNA-damaging antitumoral agent and conjugated Dbait molecules may also be simultaneously administered.

Once the treatment by radiotherapy or with the DNA-damaging antitumoral agent has begun, the treatment with the endosomolytic agent and/or conjugated Dbait molecules can continue as long as the treatment by radiotherapy or with the DNA-damaging antitumoral agent is to be applied or administered. Alternatively, the treatment with the endosomolytic agent and/or conjugated Dbait molecules can also end.

For conjugated Dbait molecules, the effective dosage of the DNA-damaging antitumoral agent employed in the combined preparation, kit or product of the invention may vary depending on the mode of administration, the condition being treated, and the severity of the condition being treated. Thus, the dosage regimen of the conjugated Dbait molecules is selected in accordance with a variety of factors including the route of administration and the patient's status. A physician, clinician or veterinarian of ordinary skill can readily determine and prescribe the effective amount of the conjugated Dbait molecules required to prevent, counter or arrest the progress of the cancer, in particular in combination with the selected DNA-damaging treatment.

For instance, for local administration (e.g., when intratumoral or subcutaneous administration is used), the efficient amount of the conjugated Dbait molecules is at least 0.01 mg per 1 $cm^3$ of tumor, preferably 0.1-40 mg per 1 $cm^3$ of tumor, most preferably 1-20 mg per 1 $cm^3$ of tumor. The efficient amount can be administered in a daily treatment protocol (e.g., 5 days per week for 3 to 6 consecutive weeks or 3 times a week for 3 to 6 consecutive weeks). Alternatively, an efficient amount of at least 0.1 mg per 1 $cm^3$ of tumor, preferably 0.1-40 mg per 1 $cm^3$ of tumor, most preferably 1-20 mg per 1 $cm^3$ of tumor, can be administered in a weekly treatment protocol for 3-6 consecutive weeks, for instance. When other administration routes are used, one skilled in the art can adapt the amount in order to obtain an efficient amount of the conjugated Dbait molecules in the tumor of at least 0.01 mg per 1 $cm^3$ of tumor, preferably 0.1-40 mg per 1 $cm^3$ of tumor, most preferably 1-20 mg per 1 $cm^3$ of tumor, in particular in a daily treatment protocol or in a weekly treatment protocol. For instance, for a systemic route, the efficient amount or unit dosage of the conjugated Dbait molecules may be 0.1 to 100 mg, preferably 4 to 40 mg. Accordingly, for a systemic route, the efficient amount or unit dosage of the conjugated Dbait molecules may be 0.06 to 0.6 mg/kg of patient. Of course, the dosage and the regimen can be adapted by one skilled in art in consideration of the chemotherapy and/or radiotherapy regimen.

For the endosomolytic agent, in particular chloroquine or hydroxychloroquine, more preferably chloroquine, the effective dosage of the endosomolytic agent employed in the combined preparation, kit or product of the invention may vary depending on the mode of administration, the condition being treated, and the severity of the condition being treated. Thus, the dosage regimen of the endosomolytic agent is selected in accordance with a variety of factors including the route of administration and the patient's status. A physician, clinician or veterinarian of ordinary skill can readily determine and prescribe the effective amount of the endosomolytic agent required to prevent, counter or arrest the progress of the cancer, in particular in combination with the conjugated Dbait molecules and the selected DNA-damaging treatment.

In a particular embodiment, when an oral route is used and if the selected endosomolytic agent is known to be useful for treating or preventing malaria, the endosomolytic agent, in particular chloroquine or hydroxychloroquine, more preferably chloroquine, is used with the same dose and regimen as for treating or preventing malaria. For instance, if the selected endosomolytic agent is chloroquine or hydroxychloroquine, more preferably chloroquine, chloroquine or hydroxychloroquine may be administered at 100-600 mg per day, preferably 200-400 mg per day, more preferably about 300 mg per day, once, twice, three times or four times a week. In a particular embodiment, chloroquine or hydroxychloroquine may be administered at about 100 mg per day during one or two weeks or at about 300 mg, twice a week during one or two weeks.

In another particular embodiment, when a local route is contemplated, for instance a subcutaneous or intratumoral route, the endosomolytic agent, in particular chloroquine or hydroxychloroquine, more preferably chloroquine, may be used with 100-300 mg.

For radiotherapy, any radiotherapy regimen known in the art may be used, in particular stereotactic irradiation (e.g., 15 Gy) or fractionated irradiation. The use of fractionated irradiation may be particularly efficient; for instance irradiation may be applied every day or every 2-5 days, preferably every 3-4 days, for a period of one, two, three, four, five or six weeks. The irradiation may be from 1 to 10 Gy, preferably from 2 to 5 Gy, in particular 2, 3, 4 or 5 Gy. For instance, fractionated irradiation of 15×2Gy for six weeks, or 4 to 6×5Gy for two weeks may be contemplated. In a preferred embodiment, the contemplated radiotherapy is a protocol with 4 irradiations of 5 Gy for two weeks. Different regimens or conditions of combined treatments of cancer with irradiation and Dbait molecules have been tested and allowed to demonstrate that the radio-sensibilization of tumors by Dbait molecules depends on the doses of Dbait molecules but not on the irradiation doses.

For chemotherapy, the effective dosage of the DNA-damaging antitumoral agent employed in the combined preparation, kit or product of the invention or in combination with the composition of the invention may vary depending on the particular DNA-damaging antitumoral agent employed, the mode of administration, the condition being treated, and the severity of the condition being treated. Thus, the dosage regimen of the DNA-damaging antitumoral agent is selected in accordance with a variety of factors including the route of administration and the patient's status. A physician, clinician or veterinarian of ordinary skill can readily determine and prescribe the effective amount of the DNA-damaging antitumoral agent required to prevent, counter or arrest the progress of the cancer.

The treatment may include one or several cycles, for instance two to ten cycles, in particular two, three, four or five cycles. The cycles may be continued or separated. For instance, each cycle is separated by a period of time of one to eight weeks, preferably three to four weeks.

Further aspects and advantages of the present invention will be disclosed in the following experimental section, which should be regarded as illustrative and not limiting the scope of the present application. A number of references are cited in the present specification; each of these cited references is incorporated herein by reference.

EXAMPLES

A Multiscale Comparison of Distribution and Activity of Short DNA (Dbait) Complexed with Polyethylenimine (PEI) or Bound to Cholesterol Characterization of Dbait/Vector Complexes and Cell Uptake It has been shown that PEI is able to form non-covalent interpolyelectrolyte complexes with DNA, oligonucleotides and RNA. Long PEI chains are highly effective in gene transfection, but more cytotoxic. The inventors tested several PEI particle polyplexes with Dbait and compared their activity to a modified Dbait covalently linked to cholesterol (called coDbait). The coDbait was a Dbait molecule covalently bound to a fatty chain of cholesterol that was used without additional vectors. For each vector tested, the main goal of the inventors was to develop a formulation with the most homogeneous particle size distribution at the highest Dbait concentration. The diameter and surface charge of the particles were measured by dynamic laser light scattering (DLS). Using a multimodal analysis, the inventors found that branched PEI (bPEI25K) with a mean size of 25 Kd and linear PEI with a size of 22 Kd (PEI22K) or 11 Kd (PEI11K) formed complexes with Dbait with similar properties (Table 1).

TABLE 1

Fluorescence and cellular uptake of formulated Dbait

| Molecules/Methods | Chloroquine (100 mg/mL) | Dbait (μg/mL) | fluorescence[a] × 10e−6/μg/mL | MCC[b] 5 hrs | cor MCC[c] 5 hrs | MCC[b] 24 hrs | cor MCC[c] 24 hrs |
|---|---|---|---|---|---|---|---|
| — | − | | 0 | 2.78 | ND | 3.2 | ND |
| chloroquine | + | | 0 | 3.12 | | | |
| Electroporation | − | 1.6 | 6.17 | 8.72 | 1.41 | 10.79 | 1.75 |
| Electroporation | + | 16 | 6.17 | 8.6 | 1.39 | ND | ND |
| Dbait | − | 1.6 | 6 | 2.65 | 0.43 | 3.45 | 0.56 |
| Dbait/PEI11K | − | 1.6 | 1.92 | 26.46 | 13.78 | 13.26 | 6.91 |
| Dbait/bPEI25K | − | 1.6 | 3.04 | 51.62 | 16.98 | 57.98 | 19.07 |
| Dbait/PEI22K | − | 1.6 | 3.32 | 54.49 | 16.41 | 42.74 | 12.87 |
| Dbait/SuperFect | − | 1.6 | 6.41 | 220 | 34.32 | 203.78 | 31.79 |
| Dbait/SuperFect + CQ | + | 1.6 | 6.31 | 218 | 34.01 | ND | ND |
| coDbait | − | 1.6 | 3.47 | 10.02 | 2.89 | ND | ND |
| coDbait + CQ | + | 1.6 | 3.47 | 20.71 | 5.97 | ND | ND |
| coDbait | − | 16 | 3.47 | 65.74 | 18.95 | 64 | 18.44 |
| coDbait + CQ | + | 16 | 3.47 | 236.43 | 68.14 | 214.3 | 61.76 |
| coDbait | − | 32 | 3.47 | 145 | 41.79 | ND | ND |
| coDbait + CQ | + | 32 | 3.47 | 390.38 | 112.50 | ND | ND |

[a]fluorescence at FL2 value;
[b]MCC = mean cellular content FL2 value (>3 experiments);
[c]cor MCC = corrected cellular content FL2/fluorescence Different ratios of PEI on Dbait were tested. The lowest ratio leading to 100% Dbait complex was determined by gel shift assay. The N/P ratios of 6, 6 and 9 were respectively chosen for PEI11K, PEI22K and bPEI25K for further studies. Dbait-PEI complex particles were stable over a period of one hour in sucrose 10%. The highly homogenous morphology of spherical particles in the population (with sizes ranging from 125 to 140 nm) was confirmed by transmission electron microscopy (FIG. 1A). The presence of salt in the dilution buffer at concentrations exceeding 0.8 mg/mL, or prolonged storage, induced PEI complex aggregation. SuperFect complexes (60 μg SuperFect/μg Dbait) giving larger and polydisperse aggregates (>2 μm) were used as a positive control. The uncharged amphiphilic copolymer Lutrol did not form stable interacting complexes with Dbait and was used as a negative control in some experiments.

Figure 1B:
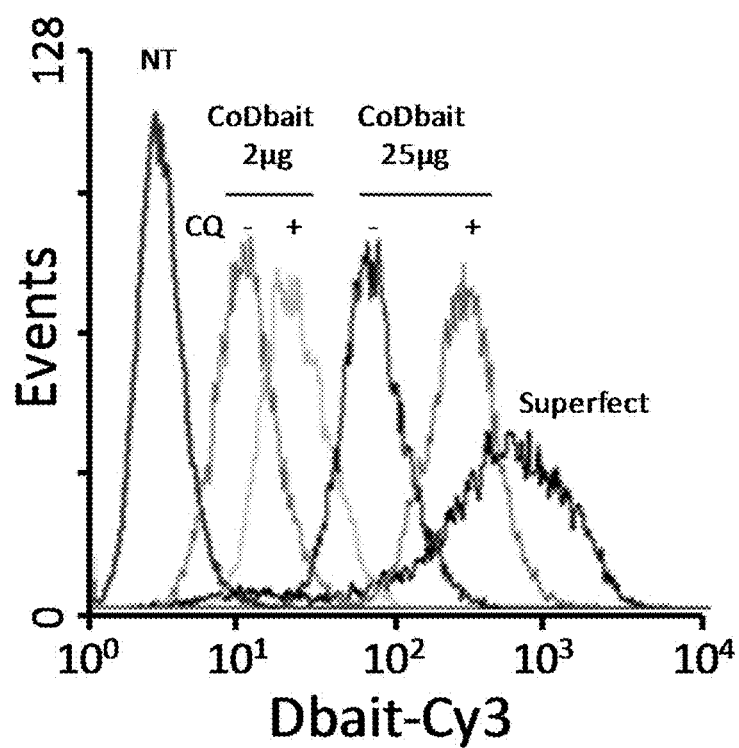

The inventors monitored the cellular uptake of the different complexes using a fluorescent cy3-modified Dbait. The initial fluorescence of the cy3-Dbait complex was monitored immediately before transfection. In PEI complexes, the Dbait fluorescence was 2 to 3-fold decreased, indicating that the compaction of the molecules with PEI might quench fluorescence (Table 1). coDbait was also less fluorescent than naked Dbait, indicating that cholesterol might interact with the cyanine on the same molecule. SuperFect or Lutrol did not affect fluorescence. Cellular content of human transfected fibroblast cells was measured by flow cytometry analysis. Fluorescence distribution of cells treated with naked Dbait or Dbait-Lutrol mixture was not different from untreated controls, indicating that Dbait molecules did not enter spontaneously into the cells. Electroporation was relatively inefficient and increasing the concentration of Dbait did not improve the transfection efficiency. All polycationic polymers (PEI and SuperFect) promoted efficient cellular uptake, but linear PEIs showed a wider distribution than Dbait/SuperFect or Dbait/PEIb25K complexes. The coDbait entered cells without the help of transfection factors but with a 10-fold lower efficiency than Dbait/PEI. Increasing the 10-15 folds the concentration of coDbait allowed efficient transfection (FIG. 1B).

Figure 2A:
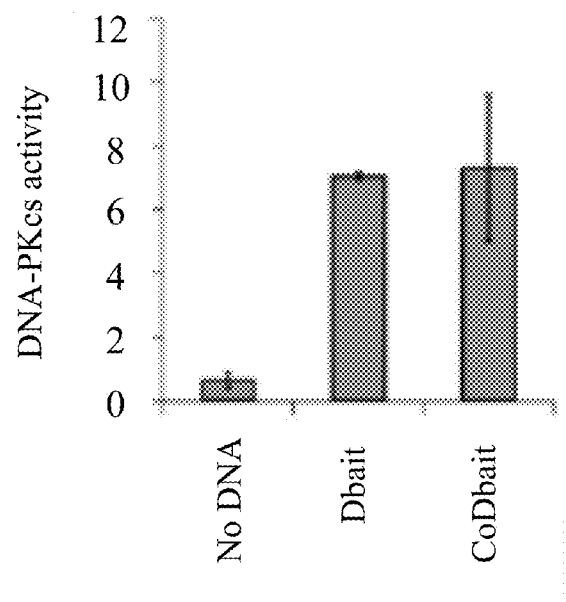
Figure 2B:
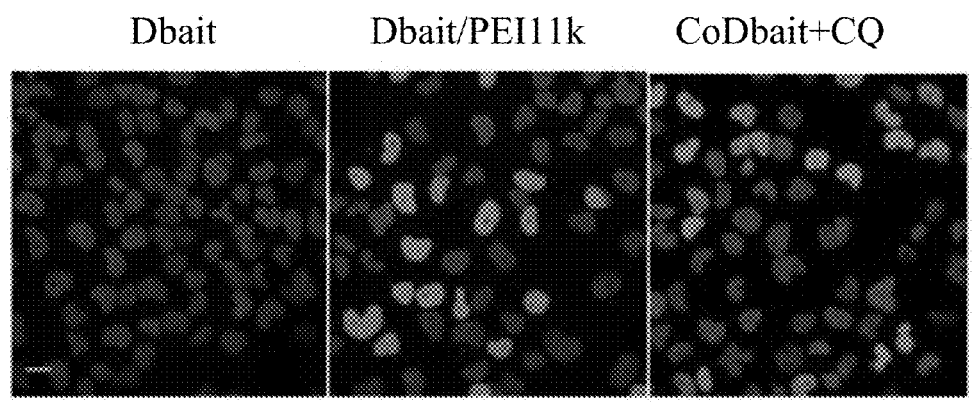

One limitation of the DNA transfer efficiency is its retention in endosomes, which prevents it from interacting with its target or being transcribed. DNA must escape from normal endosomal pathways into the cell, which leads to degradation. Therefore, the efficiency of DNA delivery is correlated not only with cellular uptake, but also with destabilization and escape from endosomes. PEI is known to have a high buffering capacity that facilitates DNA release from endosomes and lysosomes ("proton sponge hypothesis"). In contrast, coDbait requires the help of fusogenic agents such as chloroquine (CQ) to be efficiently released from the endosomes. In order to improve transfection efficiency, we added 100 µM CQ to the cells half an hour before transfection. CQ increased by 2-4 fold the cellular uptake of coDbait (FIG. 1). The amount of Dbait released into the cell was monitored by the activation of the DNA-PKcs kinase triggered by its binding to the Dbait molecules (Quanz et al., 2009, supra). Addition of cholesterol did not affect the ability of Dbait to activate purified DNA-PK (FIG. 2A). In the cell, the DNA-PKcs kinase activation was monitored by the amount of H2AX phosphorylation, which has been shown to be strictly dependent on DNA-PK. Both Dbait/PEI and coDbait induced H2AX phosphorylation in treated cells (FIG. 2B). Branched and linear PEI/Dbait complexes rapidly promoted H2AX phosphorylation (FIG. 2C) that reached a maximum 6 hours after the beginning of transfection and persisted 24 h after transfection. Dbait-induced kinase activity was very low after electroporation at any time (FIG. 2). High concentrations of coDbait were very inefficient to phosphorylated H2AX, and required at least 24 hours to reach maximal value. Addition of CQ during transfection increased DNA-PKcs activation in coDbait-transfected cells up to that observed with 10-fold less Dbait/PEI (FIG. 2C). CQ did not increase the activity in Dbait/PEI transfected cells, indicating that Dbait is efficiently released from endosomes when it is complexed to PEI. Since coDbait cellular uptake did not increase between 5 hours and 24 hours after transfection, the slow activation of DNA-PK by coDbait reveals its slow release from endosomes.

Cellular Uptake and Overall Toxicity in Zebrafish Early Embryos

Analyzing Dbait uptake and activity in cell cultures does not allow conclusions to be made about the drug diffusion, cellular uptake and activity in the whole organism. The inventors assessed this issue by injecting Dbait-cy3, either naked or with adjuvant, into the intercellular space of 1000-cell stage (stage 1K) zebrafish embryos (Kimmel et al., 1995, Dev Dyn 203:253-310). This protocol allowed the in vivo observation by confocal microscopy of Dbait-cy3 distribution at the cellular and sub-cellular level as well as its activity on the fast-dividing cells of the early zebrafish embryo. Naked Dbait-cy3 injected at the animal pole of stage 1K embryos rapidly diffused throughout the whole blastoderm and was no longer detected by 15 minutes after injection. The addition of Lutrol allowed Dbait to be retained in the extracellular space around the injection point but did not facilitate cellular uptake. In the presence of SuperFect or PEI, numerous fluorescent patches were observed inside the cells, indicating efficient cellular uptake. coDbait-cy3 showed another type of behavior with a strong and persistent staining of plasmic membranes together with patchy intracellular fluorescence. Embryos incubated with CQ prior to injection converted the large coDbait fluorescent patches into diffuse intracellular distribution.

Figure 3D:
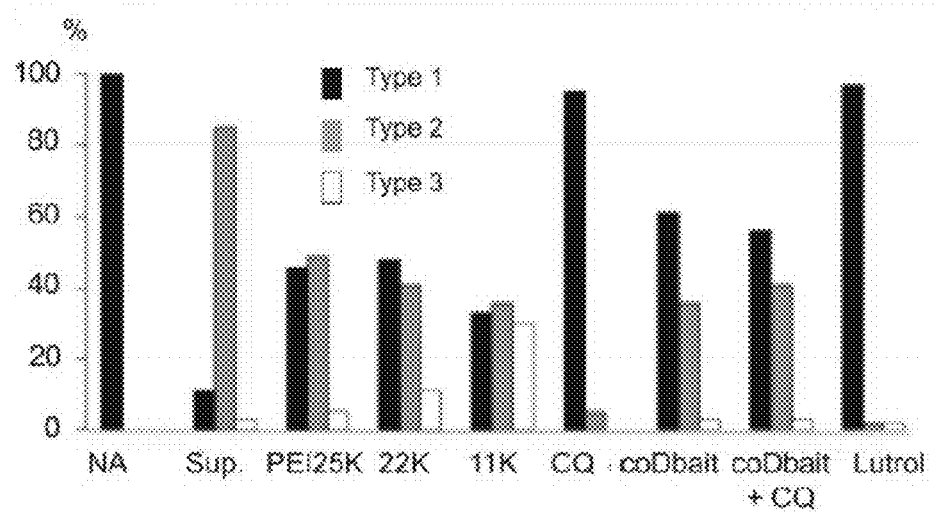

The observation of phenotypic effects 20 hours after injection allowed assessment of Dbait activity and treatment overall toxicity. Dbait fluorescence was detected 24 hours after injection in the head cells of larvae (FIG. 3A-C), which according to the zebrafish fate map development (Woo et al., 1995, Curr Opin Genet Dev 5:439-443) derived from the injected area at the animal pole of pre-gastrulation embryos. Injection of Dbait without adjuvant (NA) or combined with Lutrol (Lu) showed no effect on development (FIG. 3D), correlating with the poor intracellular uptake of Dbait described above. Addition of adjuvant led to cell death in the head and, correlating with the injected volume, extensive cell death and teratogenesis might be observed. The 24-hour phenotypes were categorized as described (FIG. 3), allowing quantification of the injected mixture's toxicity. For the same concentration of Dbait, clear differences appeared in terms of cell death and subsequent developmental abnormalities, depending on the adjuvant. Addition of SuperFect (sup) was very toxic to embryonic cells and extensive cell death at early stages resulted in a high percentage of type 2 phenotypes. Similarly, addition of PEI (25K, 22K, 11K) proved to be toxic to zebrafish blastomeres. Although less efficient than PEI addition, coDbait injection resulted in significant cell death. Embryo preincubation with CQ did not increase significantly the toxicity. Altogether, early embryonic cell death and subsequent developmental abnormalities was a fast and reliable protocol to assess Dbait+/− adjuvant's overall toxicity in zebrafish embryos. Correlation of cell death with cellular uptake suggested that anti-tumoral activity of Dbait in embryonic cells might play an important role in the toxic effect.

Local and Systemic Toxicity in Mice

To assess the consistency of cell culture, zebrafish embryos and mouse data, the inventors analyzed the tolerance of nude mice's skin to repeated administration of Dbait/PEI11K, Dbait/PEI22K, Dbait/bPEI25K, and coDbait. The toxicity of the different formulations of Dbait was analyzed after 3 daily subcutaneous (SC) injections. All the Dbait/PEI showed high toxicity with injections that were tolerated at 3.75 mg/kg but started at 5 mg/kg to trigger local inflammation associated with local necrosis and ischemia that rapidly disappeared with the arrest of the treatment.

Intravenous (IV) injection toxicity gave similar results: the Dbait/PEI intravenous injections were lethal at 3 mg/kg with death occurring during injection, probably by blood clogging. Slow injections by perfusion (0.4 µL/mn) increased tolerance up to 6 mg/kg Dbait/PEI (6 nmoles/injection), confirming that most of the IV toxicity is due to local concentration at the bolus injection site. coDbait with or without CQ did not show any toxicity at all tested doses (up to 800 mg/kg/injection; 800 nmoles/injection) whatever the route used: SC, IV bolus or IV perfusion.

Antitumoral Activity in Xenografted Tumours

The antitumoral effect of formulated Dbait was tested in combination with radiotherapy on SK28 xenografted human melanoma. Dbait/vector complexes were administered 5 hours before each irradiation using intratumoral injections.

Figure 4:
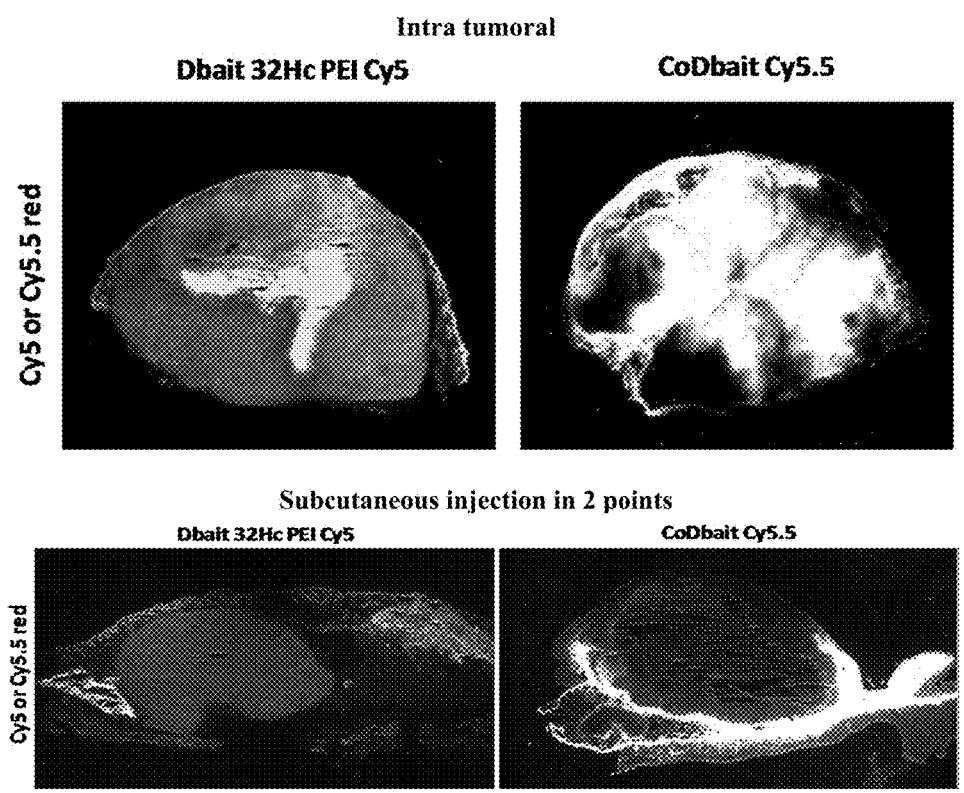
FIG. 4: Diffusion and activity in tumors. Tumors were injected with 1.6 μg Dbait-cy5.5/PEI or 16 μg coDbait-cy5.5 (1/10 of cy5.5 labeled coDbait+9/10 unlabeled coDbait in order to keep similar fluorescence intensity) and analyzed the following day for fluorescence distribution and DNA-PKcs activity. Diffusion of fluorescent Dbait after two types of injections: one intratumoral injection or two subcutaneous injections.

Though drug administration by intratumoral injection (IT) has been used in many trials, it is currently advised to avoid that route of delivery in clinical assays. The inventors investigated how Dbait/PEI11k or coDbait could be administered by subcutaneous injection (SC) in the area next to the tumor. Several clinical assays have successfully used this route of administration. The inventors first compared the diffusion of the molecules in tumors treated by one intratumoral injection or two subcutaneous injections performed at opposite sides of the tumor (FIG. 4). Fluorescent Dbait complexed to PEI11k tended to form aggregates at the site of injection and diffused progressively to the edge of the tumor. In contrast, coDbait showed a more even distribution around the injection, whether inside the tumor or in its vicinity. SC injections of Dbait/PEI11k or coDbait were slightly less efficient than IT injections in terms of tumor growth control (Table 2). However, increasing the number of injection sites should allow significant improvement of tumor growth control without adding local toxicity.

Survival of five groups of nude mice bearing SK28 melanoma xenografts has been studied. Group 1) untreated mice (n=16); Group 2) irradiated mice (IR, n=12); Group 3) irradiated mice with intraperitoneally injected 1 mg chloroquine (CQ, IR, n=10); Group 4) treated mice by intratumorally injected 0.6 mg DT01 (also called coDbait) and irradiated 5 hours later (DT01, IR, n=11); and Group 5) pretreated mice with intraperitoneally injected 1 mg chloroquine 2 hours prior to intratumoral injection of 0.6 mg DT01 (also called voDbait) and irradiated 5 hours later (DT01, CQ, IR, n=13).

Figure 5:
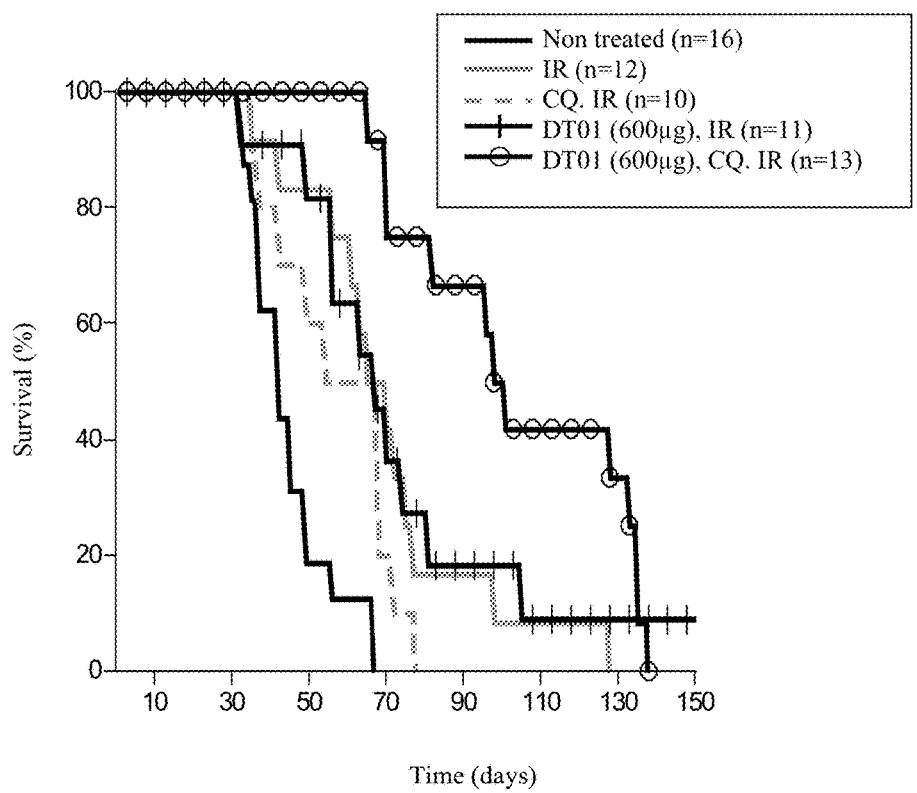
FIG. 5: Survival of 5 groups of nude mice bearing SK28 melanoma xenograft: 1) untreated (n=16); 2) irradiated (IR, n=12); 3) irradiated with intraperitoneally injected 1 mg chloroquine (CQ, IR, n=10); 4) treated by intratumorally injected 0.6 mg DT01 (also called CoDbait) and irradiated 5 hours later (DT01, IR, n=11) and 5) pretreated with intraperitoneally injected 1 mg chloroquine 2 hours prior intratumoral injection of 0.6 mg DT01 (also called CoDbait) and irradiated 5 hours later (DT01, CQ, IR, n=13).

Results are presented in FIG. 5.

With 0.6 mg coDbait administered intratumorally, pretreatment by chloroquine remarkably radiosensitized and increased the survival (group 5) as compared to radiotherapy alone (group 2), while neither coDbait (group 4) nor CQ (group 3) showed significant radiosensitization. The extent of radiosensitization of group 5 was similar to that treated by 0.06 mg Dbait formulated with polyethylenimine (PEI) at the ratio N/P=6.

Figure 6:
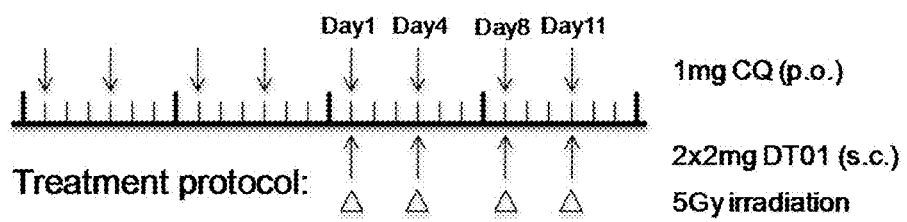
FIG. 6. Study of tumor growth of melanoma SK28 grafted onto nude mice. Top: treatment protocol: 4 treatments of DT01 (also called CoDbait) combined with 4 irradiation (RT) sessions in two weeks. 4 mg DT01 were subcutaneously injected at two opposite points separated by 5 mm from the tumor border. Animals were pre-treated before beginning of treatment and during the DT01+RT treatment with 1 mg chloroquine (CQ) twice a week by oral administration (p.o.)*. Middle: Mean value of tumor growth of various animal groups; Untreated or CQ: untreated or only treated by CQ (n=11); RT or CQ+RT: irradiated with or without a co-treatment of chloroquine (n=16); DT01+RT: treated by DT01 and irradiation (n=10); DT01+CQ+RT: treated by DT01 with chloroquine and irradiation (n=12). Bottom: Details of groups DT01+RT and DT01+CQ+RT. Each curve corresponds to one tumor growth.
Figure 6:
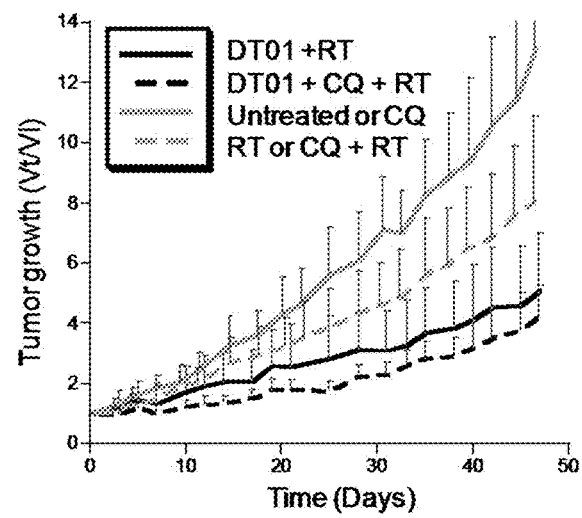
Figure 6:
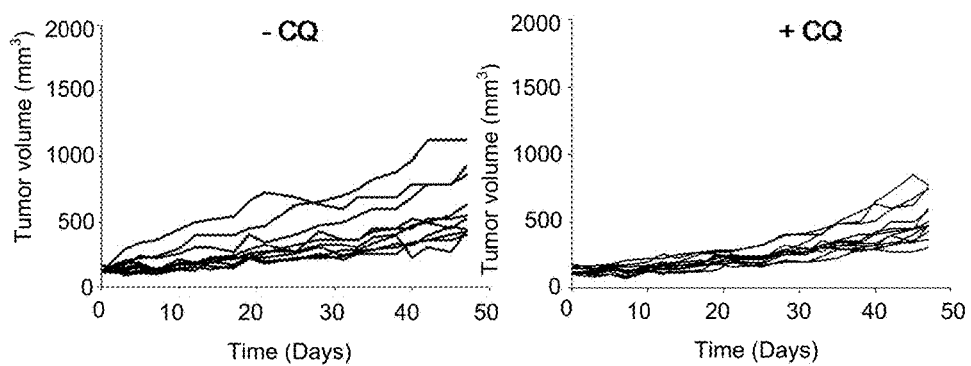

An administration regimen based on a subcutaneous injection of coDbait has also been evaluated on nude mice bearing SK28 melanoma xenografts. This regimen is schematically disclosed in FIG. 6. In brief, this regimen includes four combined treatments by coDbait and irradiation in two weeks. In particular, 4 mg of coDbait were subcutaneously injected at two opposite points separated by 5 mm from the tumor border. In addition, the animals have been pretreated with 1 mg of chloroquine (CQ) and further treated with CQ at the same dosage during the treatment with coDbait and irradiation. Tumor growth was evaluated after this administration regimen and the results are given in FIG. 6.

It has been observed that the lowest tumor growth is observed with the cotreatment of coDbait and irradiation with chloroquine after a pretreatment with chloroquine. In addition, the group co-treated with chloroquine showed more homogenous results than those without chloroquine treatment.

Conclusion

In the present study, the inventors used a set of assays to guide development of administration protocols and drug formulation. These assays allowed the comparison of different formulations of Dbait before performing preclinical assays on mice. Cellular and zebrafish embryo assays were used to assess the efficiency of Dbait cellular uptake, a prerequisite step in the antitumoral drug effect, and to select the most appropriate protocols and formulations for preclinical studies on mammals. Overall toxicity in zebrafish embryos did not correlate with toxicity in mice's skin or after systemic injection. In particular, the high toxicity of coDbait in zebrafish embryos indicated that most of the cells contacting the drug probably died, whereas mice's skin did

TABLE 2

Xenografted mice's survival after irradiation associated with various treatments

| Dbait/Vector complexes | Dbait concentration | mode of admin.[a] | Nb. mice | Cured mice[b] | Median survival time | Relative risk (p value) | Mean TGD | SD TGD | Mean % TGD[c] |
|---|---|---|---|---|---|---|---|---|---|
| Mock | — | IT | 79 | 2 | 72 | — | 11 | 15 | 160 |
| Dbait | 6 × 60 µg (3 nmol) | IT | 6 | 0 | 63 | 1.40 (p < 0.41) | 3 | 8 | 114 |
| Dbait/PEI11k | 6 × 60 µg (3 nmol) | IT | 38 | 3 | 123 | 0.26 (p < 2.69.10−8) | >40 | 27 | 313 |
| Dbait/PEI22k | 6 × 60 µg (3 nmol) | IT | 10 | 2 | >150 | 0.09 (p < 4.62.10−6) | >63 | 40 | 436 |
| Dbait/PEIb25k | 6 × 60 µg (3 nmol) | IT | 19 | 4 | >150 | 0.13 (p < 3.73.10−8) | >60 | 35 | 419 |
| Dbait/Lutrol | 6 × 60 µg (3 nmol) | IT | 10 | 0 | 72 | 1.2 (p < 0.56) | 5 | 5 | 128 |
| Dbait/PEI11k | 6 × 150 µg (7.5 nmol) | SC | 12 | 0 | 135 | 0.34 (p < 1.05.10−3) | 22 | 15 | 216 |
| CQ | — | IT | 6 | 0 | 68 | — | 8 | 6 | 142 |
| coDbait + CQ | 6 × 600 µg (30 nmol) | IT | 13 | 0 | 98 | 0.23 (p < 4.02.10−4) | 42 | 25 | 323 |
| coDbait + CQ | 6 × 1.2 mg (60 nmol) | SC | 16 | 0 | 101 | 0.22 (p < 1.05.10−3) | >22 | 23 | 218 |

[a] mode of administration: IT, intratumoral; SC, subcutaneous
[b] cured mice are animals with no recurrence within 300 days following treatment
[c] TGD calculation and statistical analysis are described in Material and Methods not show any reaction to injections of high doses of coDbait. This difference suggests that toxicity in zebrafish early embryos is an indicator of tumor sensitivity rather than healthy tissue sensitivity. Actually, Dbait molecules have been shown to be specifically toxic in tumors but not in normal skin (Quanz et al., 2009, supra). Dbait/PEI (5 µM) and coDbait (50 µM)+CQ that triggered comparable DNA-PKcs activation in cell cultures had a similar toxic effect on zebrafish embryos (FIG. 3D) and displayed significant antitumoral activity on mouse tumors (Table 2, FIGS. 5 and 6). This observation is consistent with the sensitivity to antitumoral activity of zebrafish embryonic cells that share characteristic properties with tumor cells, including mitotic index and biochemical and phenotypic traits. In agreement with this hypothesis, the inventors recently demonstrated Dbait antiproliferating activity by direct intracellular injection of naked Dbait into zebrafish blastomeres between the 1 and 16-cell stage.

PEI polymers were among all tested adjuvant molecules, the most efficient in forming Dbait complexes. Their use was however limited by their toxicity on tissues as well as in the blood system. Local toxicity was partly overcome by slow administration (perfusion) and by splitting the injected doses between different injection sites. But the covalent combination of cholesterol and Dbait provided the best alternative for Dbait delivery to the cells without adjuvant addition. Indeed, the lack of toxicity within the range of tested doses suggests that this molecule might prove to be useful despite the highest doses required for antitumoral effect. The doses of 3 nmoles and 30 nmoles per injection of Dbait/PEI11K and coDbait respectively doubled the delay in tumour growth induced by irradiation alone. The respective toxicity of both formulations (6 nmoles and >800 nmoles) gave a relative ratio of efficiency dose/toxicity dose of 0.5 for Dbait/PEI11K and <0.037 for coDbait, indicating that coDbait is a very good candidate for clinical trials.

Materials and Methods
Dbait and Particle Formation

Dbait and coDbait molecules were obtained by automated solid-phase oligonucleotide synthesis from Eurogentec (Seraing, Belgium) or from Agilent Technologies Nucleic Acid Solution Division (Boulder, USA) as described previously (Quanz et al., 2009, supra). They were purified by denaturing reverse-phase HPLC and/or HPLC-IEX. Some Dbait derivatives were labeled with the fluorophores Cy3 ($\lambda_{excitation}$=540 nm; $\lambda_{emission}$=560 nm) or Cy5.5 ($\lambda_{excitation}$=X nm; $\lambda_{emission}$=X nm). Linear PEI (11 kDa and 22 kDa) were from Polyplus-transfection (Illkirch, France) and provided as a ready-to-use solution of 300 mM nitrogen concentration. Branched bPEI25 kd was purchased from Sigma-Aldrich (Saint Quentin, France). Lutrol was purchased from In-Cell-Art (Nantes, France). Dbait and PEI solutions (stock PEI) were diluted in 10% sucrose or 150 mM NaCl (for in vitro transfection experiments) to obtain various ratios of vector/Dbait. The ratio of PEI/Dbait (or ratio N/P) was determined according to the number of amine nitrogen for PEI and phosphate for Dbait. Typically, for 300 µL of complexes at 0.6 mg/mL and N/P 6, Dbait (180 µg, 0.54 µmol of phosphate) and the desired amount of polymer solution (11.4 µL of PEI stock solution contains 0.3 µmol of amine nitrogen) were each diluted into 150 µL (10% sucrose). SuperFect/Dbait particles were prepared according to the manufacturer (Qiagen, Courtaboeuf, France) in a ratio of 10 µl SuperFect per µg DNA. The complexation of vector/Dbait was analyzed by the agarose gel electrophoresis method. The samples (18 µL) were mixed with bromophenol blue dye (1 µL) and then loaded on 1.5% agarose gel into the electrophoresis chamber containing TAE buffer 1× (40 mM Tris-acetate, pH 8.3, 1 mM EDTA). The gel was run at 100 volts for 30 min. Then the gel was stained with ethidium bromide (EtBr) for 15 minutes and the bands observed under UV light.

Cell Culture, Dbait Molecules and Transfection

The Dbait molecules were made by automated solid-phase oligonucleotide synthesis. Sequence is 5'-GCTGTGC-CCACAACCCAGCAAACAAGCCTAGA-(H)-TCTAG-GCTTG TTTGCTGGGTTGTGGGCACAGC (SEQ ID NO: 4) where H is a hexaethyleneglycol linker. Studies on cells in culture were performed using SV40 transformed fibroblasts MRC-5. Cells were grown at 37° C. in monolayer cultures in complete DMEM (Gibco, Cergy-Pontoise, France) with 10% FCS and antibiotics (100 µg/mL streptomycin and 100 µg/mL penicillin) under conditions of 100% humidity, 95% air and 5% $CO_2$. Unless otherwise specified, transfections were performed in 1.2 mL MEM medium without serum in 60 mm diameter plates. Transfection with jetPEI (Polyplus-transfection, Illkirch, France) was performed at an N/P ratio of 6 according to the manufacturer's instructions. Briefly, Dbait was diluted in 150 mM NaCl and gently mixed with an equal volume of PEI in 150 mM NaCl and added to DMEM medium without serum. coDbait was directly added to DMEM medium without serum. Transfection of Dbait molecules was performed with SuperFect reagent in 1.2 mL DMEM medium with serum (in 60 mm diameter plates) for 5 hours and then cells were left to recover for 1 hour if not indicated otherwise. For electroporation, $1.2 \times 10^6$ cells were transfected with 2 µg Dbait using the Gene Pulser II (Bio-Rad, Marnes-la-Coquette, France). At the end of the 5 h transfection (time zero), medium was replaced by complete medium and cells were grown for the indicated time before being analyzed. Chloroquine (50 µM) was added 30 min before transfection.

Flow Cytometry

Cells were transfected with different complexes with Dbait-cy3 for 5 h and allowed to grow 5 hours or 24 hours, then rapidly washed with PBS. Cells were directly analyzed by flow cytometry. For immunofluorescence detection by flow cytometry, the cells were fixed in 2% paraformaldehyde for 10 min prior to immunodetection. Note that permeabilization treatment removed most of the Dbait, impairing immunofluorescence detection and Dbait detection on the same cells. Cells were fixed for 15 min in 4% formaldehyde, permeabilized in 0.2% Triton X-100 for 1 hour, blocked with 2% BSA and incubated with primary antibody for 2 hours on ice with mouse monoclonal antibodies anti γ-H2AX (Upstate Biotechnology, Temecula, Calif., USA) and revealed with secondary antibodies conjugated with Alexa-488 (Molecular Probes, Eugene, Oreg., USA) and Texas Red (Rockland, Gilbertsville, Pa., USA) at a dilution of 1/200 for 30 min at RT. Cells were washed with PBS and resuspended in PBS with 50 µg/mL propidium iodide, 25 µU/ml RNaseA. Cells were analyzed by a FACSCalibur flow cytometer (BD Biosciences, Franklin Lakes, N.J., USA) and data was analyzed using BD CellQuest Pro (BD Biosciences) and the free WinMDI 2.8 (Scripps Research Institute, La Jolla, Calif., USA) software.

Zebrafish Husbandry, Embryo Collection and Treatment

Zebrafish eggs were obtained from natural spawning of wild type or transgenic (βactin:egfp-ras) fish lines. Narishige (MN 153) micromanipulator fixed on a dissecting scope with epifluorescence illumination (Leica MZ16F) and air injector (Eppendorf FemtoJet) were used to perform Dbait injection at cell stage 1K. Glass capillaries (Harvard Apparatus GC100-10) were pulled with a KopF vertical pipette puller (KopF 720) to make injection needles. 2 to 5 nl of Dbait solution were injected at the animal pole of embryos in cell cycle 10 and immediately processed for confocal laser scanning microscopy imaging (upright Leica SP2) with 40×/0.8 NA water dipping lens objective. Imaging was performed by simultaneous 480 nm (eGFP) and 561 nm (cy3) excitation. Embryos were further grown at 28.5° C. until 24 hpf. One-day-old larvae were observed under the dissecting stop and phenotypes categorized as described in FIG. 3. Chloroquine treatment prior to injection consisted of 2 hours of incubation in embryo medium (The Zebrafish Book) with 50 chloroquine. Dbait (coDbait)-cy3 50 µM was injected either alone or in combination with PEI25K (ratio N/P=9), PEI11K (ratio N/P=6), or SuperFect (10 µg Dbait).

Dbait and Irradiation Treatments in Mice

SK28 or U87G xenograft tumors were obtained by injecting $10^6$ tumor cells into the flanks of adult female nude mice (Charles River strain; L'Arbresle, France). The animals were housed in the laboratory at least one week prior to commencing experiments. There were 5-6 animals per cage under controlled conditions of light and dark cycles (12 hrs:12 hrs), relative humidity (55%) and temperature (21° C.). Food and tap water were available ad libitum. After approximately 12 days, when the subcutaneous tumors measured 150-200 $mm^3$, the mice were separated into homogeneous groups of at most 12 each to receive different treatments. Irradiation was performed in a $^{137}Cs$ unit (0.5 Gy/min) with a shield designed to protect about two-thirds of the animal's body. Doses were controlled by thermoluminescence dosimetry. A total dose of 30 Gy was delivered in 6 sessions at intervals of three sessions of 5 Gy per week during two weeks. Dbait molecules were prepared in 100 µL of 10% sucrose as previously described for in vitro studies except that PEI mixtures were performed without NaCl (Polyplus-transfection, Strasbourg, France). The Dbait mixtures were incubated for 15 min at room temperature before injection. CoDbait was diluted in 10% sucrose at the required concentration. Intratumoral injections of the indicated amount of Dbait were performed 5 h before each radiotherapy session. Mock treated animals were injected with 100 µL of 10% glucose according to the protocol of the associated assays. Tumor size was assessed by caliper measurements every three days and size was calculated by the formula (2×length×$width^2$). Mice were weighed and pictures of tumors were taken every week. For ethical reasons, the animals were sacrificed when their tumors reached 2,000 $mm^3$. The end point used in survival analysis was death day. The Local Committee on Ethics of Animal Experimentation (Orsay, France) approved all experiments.

Statistical Analysis

Descriptive analyses of the tumor response were performed for each treatment and each tumor type. Day 1 was the day of the first treatment session. All animals were followed for at least 150 days. Median lifetime was estimated according to the Kaplan-Meier method. Tumor growth delay (TGD) was calculated by subtracting the mean tumor volume quadrupling time of the control group from tumor volume quadrupling times of individual mice in each treated group. The mean TGD was calculated for each treated group using the individual measurements. Overall survival curves were assessed by Kaplan-Meier estimates and compared using the non-parametric LogRank test since the data do not follow a normal distribution. The analysis was performed using statEL software (ad Science, Paris, France). A global LogRank was first performed for each group with the same tumor type. Then treatments with Dbait were compared to the mock-treated controls. The number of animals (n), the relative risk (RR) and the p value are reported in Table 2. All tests were considered significant at the 0.05 significance level.

Physico-Chemical Properties of Formulated Dbait Particles

The particle size of vector/Dbait was determined by dynamic light scattering (DLS) on the Zetasizer Nano Series (Malvern Instruments, Paris, France) with these specifications: medium viscosity: 1.150 cP, refractive index: 1.45, scattering angle: 90°, temperature: 25° C. Data are the mean of 3-5 measures per sample with each measure averaging the data of 10-15 sub-runs. Data were analyzed using the multimodal number distribution software supplied with the instrument. For the zeta-potential measurement, particles were diluted in 10% sucrose/10 mM NaCl to give a final Dbait concentration of 0.1 mg/mL and were measured with the following specifications: 3 measurements, medium viscosity: 1.054 cP, medium dielectric constant: 79, temperature: 25° C.

| Cationic polymers | Ratio[a] (w/w) | Size[b] (nm) | Zeta[c] (mV) | Pdl | $[C]_{max}$ (mg/mL) | supplier |
|---|---|---|---|---|---|---|
| Superfect | — | >1000 | — | 1 | nd | Qiagen |
| bPEI25K | 2.1 | 175 ± 51 | +40 | 0.11 | 1.5 | Sigma-Aldrich |
| PEI22K | 1.4 | 133 ± 25 | +46 | 0.17 | 1.0 | Polyplus-transfection |
| PEI11k | 1.4 | 125 ± 13 | +30 | <0.2 | 0.8 | Polyplus-transfection |

[a] weight ratio at which maximum Dbait activity is observed
[b] Mean diameter (+/− SD) as determined by dynamic light scattering (see supplementary Material and Methods).
[c] Particles in sucrose 1%, 10 mM NaCl Transmission Electron Microscopy Samples were prepared for transmission electron microscopy by negative staining with uranyl acetate. A drop of sample (10 µL) was deposited on the grid (formvar/carbon on 200 mesh copper, Agar Scientific) and left for 3 minutes before removing excess liquid with blotting paper. Then the complexes were stained with 10 µL of aqueous uranyl acetate (2%) for 2 min and the excess was removed with blotting paper. Observations were performed with a Jeol JEM-100S Electron Microscope.

Alternative Conjugated Dbait Molecules

Alternative conjugated Dbait molecules have been prepared and are described as follows:

Conjugated molecules of formula (IIe)

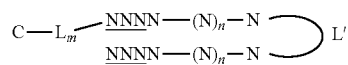

with

| Compound | C-Lm | L' | Measured mass (MALDI-TOF) |
|---|---|---|---|
| 0902 | Cholesterol-triethyleneglycol | hexaethyleneglycol | 20830.5 |
| 0903 | 1,2-di-(9Z-octadecenoyl)-sn-glycero-3-phosphoethanolamine-N-[4-(p-phenyl-3-((6-phosphohexylthio)-succinimido))butyramide] | hexaethyleneglycol | 21306.9 |
| 0904 | N-octadecyl-hexylthioamide | hexaethyleneglycol | 20411.6 |
| 0905 | N-hexyl-folic acid-amide | hexaethyleneglycol | 20739.2 |

Conjugated molecules of formula (Ie)

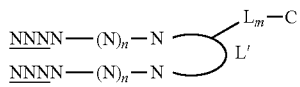

with

| Compound | C-Lm | L' | Measured mass (MALDI-TOF) |
|---|---|---|---|
| 0813 | Cholesterol-triethyleneglycol | N-(5-hydroxymethyl-6-phosphohexyl)-11-(3-(6-phosphohexythio)succinimido))undecamide | 21127.7 |
| 0815 | Cholesterol-dihexylsulfide | 1,3-bis-[5-hydroxylpentylamido]propyl-2-(6-phosphohexyl) | 21454.0 |

Figure 7:
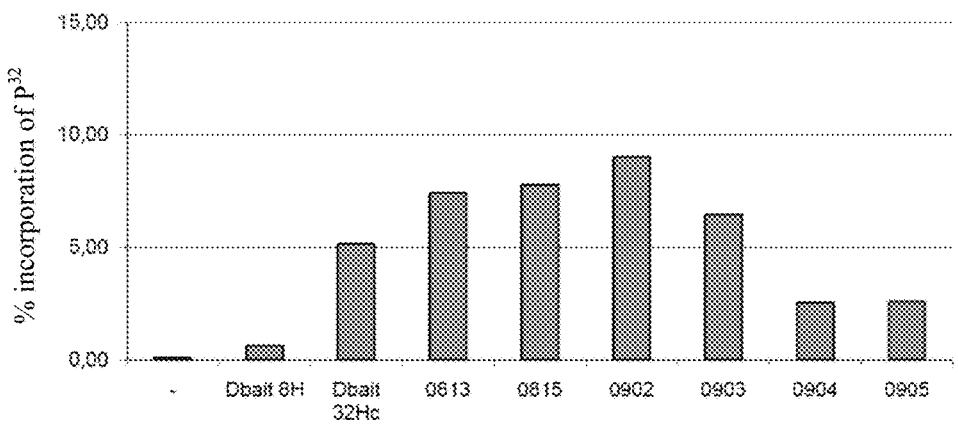
FIG. 7: DNA-PK activity was monitored using the SignaTECT DNA-dependent Protein Kinase Assay System kit (Promega, Madison, Wis., USA). The biotinylated peptide substrate, 50 units of DNA-PK (Promega, Madison, Wis., USA) and 500 nM various Dbait molecules were incubated for 5 min at 30° C. with (γ-32P) ATP according to the manufacturer's instructions. The biotinylated substrate was captured on a streptavidin membrane, washed and counted in a scintillation counter. Percentage of phosphorylation was calculated by dividing the bound radioactivity by the total count of $(\gamma\text{-}^{32}P)$ ATP per sample. Dbait32Hc is an unconjugated Dbait molecule. 0813, 0815, 0902, 0903, 0904 and 0905 are conjugated Dbait molecules (cf. Tables of "Alternative conjugated Dbait molecules"). Dbait8H is a short (8-bp) Dbait used as a negative control of DNA-PK activity.

The activity of these alternative conjugated Dbait molecules has been measured through DNA PK inhibition as detailed above (FIG. 7). It has been observed that the conjugated molecules maintain their activity. In particular, the conjugation of various lipids and ligands at either the 5' end or in the loop has minor impact on the capacity of these molecules to trigger DNA-PK activity.

Figure 8:
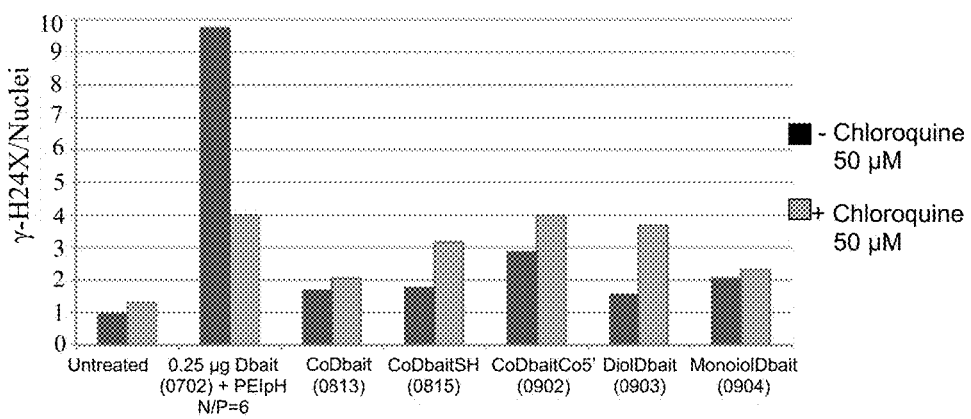
FIG. 8: Activity of Dbait molecules measured by H2AX phosphorylation. Immunodetection of the γ-H2AX in MRC5 cell line 24 hours after the transfection of various conjugated Dbait molecules (cf. Tables of "Alternative conjugated Dbait molecules") with or without prior treatment of 50 μM chloroquine. Dbait formulated by polyethylenimine (PEI) was used as a positive control.

In addition, their activity has also been measured on cell lines, with or without chloroquine, through the determination of the amount of H2AX phosphorylation as detailed above (FIG. 8). First, for the tested conjugated Dbait molecules, it has been observed that their activity is higher with a prior treatment with chloroquine. In addition, it can be noted that the conjugation of the cholesterol to the 5' end surprisingly leads to more effective molecules than the conjugation of the cholesterol in the hairpin loop (see 0902 in comparison to 0813 and 0815).

Cellular Uptake of Conjugated Dbait Molecules

Cellular uptake of the Dbait conjugated to cholesterol, in particular CoDbait, in comparison with the Dbait was measured by the inventors by flow cytometry analysis.

The results are given in the following table.

| Transfection conditions | Cy3 fluorescence intensity @5 hrs. | |
|---|---|---|
| | Median | Mean |
| Dbait-Cy3 79 nM | 3 | 3 |
| Dbait-Cy3 79 nM + Superfect | 426 | 327 |
| CoDbait-Cy3 79 nM | 10 | 10 |
| CoDbait-Cy3 79 nM + CQ 50 μM | 20 | 21 |
| CoDbait-Cy3 986 nM | 63 | 66 |
| CoDbait-Cy3 986 nM + CQ 50 μM | 239 | 236 |
| Co_siRNA_H2AX-Cy3 79 nM | 53 | 56 |
| Co_siRNA_H2AX-Cy3 79 nM + CQ 50 μM | 60 | 63 |
| Co_siRNA_H2AX 986 nM | 661 | 710 |
| Co_siRNA_H2AX-Cy3 986 nM + CQ 50 μM | 1144 | 1214 |

Flow cytometry analysis of cellular uptake in the MRC5 cell line performed at 5 hours after the beginning of treatment of various transfection conditions was as described in the table. All oligonucleotides were labeled by cyanine 3 (Cy3) dye: Dbait (Dbait-Cy3), cholesterol-Dbait (0813) (CoDbait-Cy3) and siRNA targeting H2AX with a cyanine 3 and a cholesterol at the 5' and 3' of the sense strand (Co_siRNA_H2AX: Cy3-5'-CAACAAGAAGACGC-GAAUCTT-3'-cholesterol (SEQ ID NO: 6); 5'-GAUUCGC-GUCUUCUUGUUGTT-3' (SEQ ID NO: 7). When indicated, 50 μM of chloroquine (CQ) was added prior to transfection.

We claim:

1. A conjugated nucleic acid molecule which has the following formula:

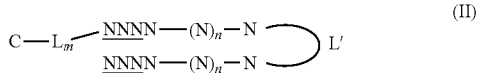

(II)

wherein N is a nucleotide, n is an integer from 15 to 195, the underlined N refers to a nucleotide having or not a modified phosphodiester backbone, L' is a linker; m is 1 and L is a linker, C is a molecule facilitating endocytosis selected from the group consisting of single or double chain fatty acids, tocopherol, folates or folic acid, cholesterol, sugar, peptide and protein, and wherein C is conjugated via L to the 5' end of the nucleic acid molecule.

2. The conjugated nucleic acid molecule according to claim 1, wherein n is 27.

3. The conjugated nucleic acid molecule according to claim 1, wherein C is selected from the group consisting of tocopherol and cholesterol.

4. The conjugated nucleic acid molecule according to claim 1, wherein L' is a loop linking the two strands of the nucleic acid molecule.

5. The conjugated nucleic acid molecule according to claim 1, wherein L' is selected from the group consisting of a nucleotide linker and a non-nucleotide linker.

6. The conjugated nucleic acid molecule according to claim 5, wherein L' is a non-nucleotide linker selected from the group consisting of abasic nucleotide, polyether, polyamine, polyamide, peptide, carbohydrate, lipid, polyhydrocarbon and polymeric compounds.

7. The conjugated nucleic acid molecule according to claim 5, wherein L' is selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane.

8. The conjugated nucleic acid molecule according to claim 1, wherein L is selected from the group consisting of aliphatic chain, polyether, polyamine, polyamide, peptide, carbohydrate, lipid, polyhydrocarbon, polymeric compounds and compounds incorporating a disulfide linkage, a protected disulfide linkage, an amide linkage, an acid labile linkage, an ester linkage, an ortho ester linkage, a phosphonamide linkage, a biocleavable peptide linkage, an azo linkage and an aldehyde linkage.

9. The conjugated nucleic acid molecule according to claim 8, wherein L is selected from the group consisting of an oligoethylene glycol and a dialkyl-disulfide.

10. The conjugated nucleic acid molecule according to claim 1, wherein the molecule is

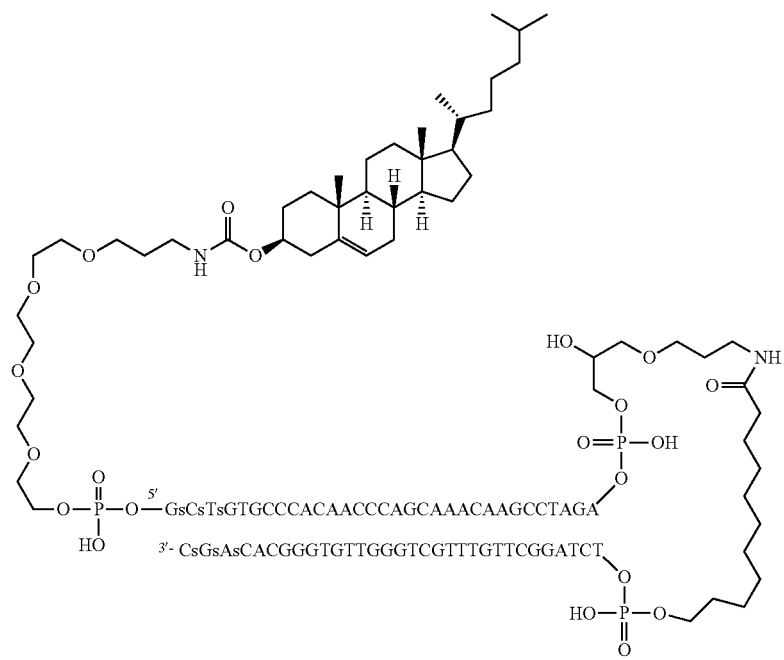

with 3 phosphorothioate internucleotide linkages at each of the 5' and the 3' ends.

11. A pharmaceutical composition comprising a conjugated nucleic acid molecule according to claim 1.

12. The pharmaceutical composition according to claim 11, wherein said composition further comprises a DNA-damaging anti-tumoral agent and a pharmaceutically acceptable carrier.

13. A kit comprising a conjugated nucleic acid molecule according to claim 1 and a DNA-damaging anti-tumoral agent, as a combined preparation for simultaneous, separate or sequential use.

14. A method for treating a cancer in a subject in need thereof, comprising administering an effective amount of conjugated nucleic acid molecule of claim 1.

15. The method according to claim 14, wherein the treatment further comprises radiotherapy or chemotherapy, optionally with a DNA damaging antitumoral agent.

* * * * *

UNITED STATES PATENT AND TRADEMARK OFFICE
CERTIFICATE OF CORRECTION

Page 1 of 2

PATENT NO. : 10,363,317 B2
APPLICATION NO. : 15/632951
DATED : July 30, 2019
INVENTOR(S) : Jian-Sheng Sun, Marie Dutreix and Maria Quanz It is certified that error appears in the above-identified patent and that said Letters Patent is hereby corrected as shown below:

In the Specification

Column 3,
Line 15, "plasma DNA" should read --plasmid DNA--.

Column 13,
Line 67, "polyhydrorarbons," should read --polyhydrocarbons,--.

Column 15,
Line 63, "phosphonannde" should read --phosphonamide--.

Column 16,
Line 10, "CO–N–(CH$_2$–CH$_2$–O)$_4$" should read --CO–NH–(CH$_2$–CH$_2$–O)$_4$--.

Column 17,
Line 43, "NNNN–(N)$_r$–N" should read --NNNN–(N)$_n$–N--.

Column 21,
Lines 58-67,

"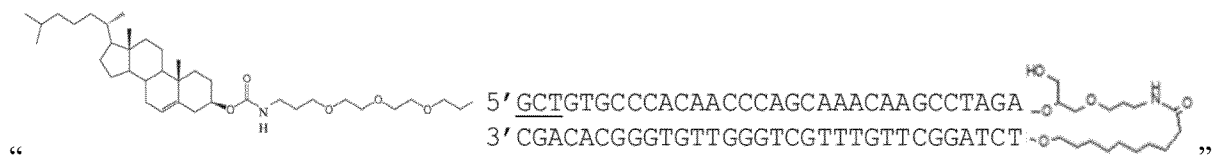"

should read

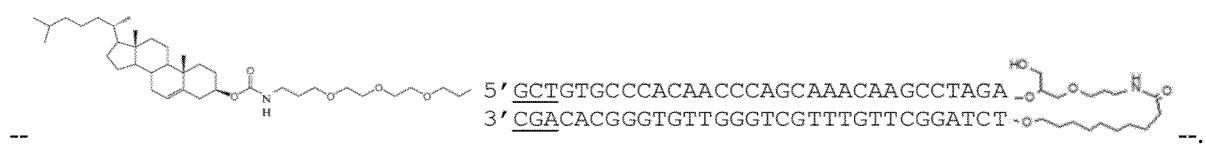
--.

Signed and Sealed this
Sixteenth Day of June, 2020

Andrei Iancu
*Director of the United States Patent and Trademark Office*

CERTIFICATE OF CORRECTION (continued)
U.S. Pat. No. 10,363,317 B2

Column 40,
Line 54, "25 µU/ml" should read --25U/ml--.

Column 41,
Line 12, "50 chloroquine." should read --50 µM chloroquine.--.
Line 14, "(10 µg Dbait)." should read --(10 µl/1 µg Dbait).--.